(12) United States Patent
Kitsunai

(10) Patent No.: US 12,251,076 B2
(45) Date of Patent: Mar. 18, 2025

(54) CENTRAL CONTROL APPARATUS, CENTRAL CONTROL SYSTEM, AND CONTROL METHOD FOR CONTROLLED DEVICES

(71) Applicant: OLYMPUS CORPORATION, Tokyo (JP)

(72) Inventor: Akane Kitsunai, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 674 days.

(21) Appl. No.: 17/375,114

(22) Filed: Jul. 14, 2021

(65) Prior Publication Data

US 2021/0338041 A1    Nov. 4, 2021

Related U.S. Application Data

(63) Continuation of application No. PCT/JP2019/001326, filed on Jan. 17, 2019.

(51) Int. Cl.
| | |
|---|---|
| *G06F 3/048* | (2013.01) |
| *A61B 1/00* | (2006.01) |
| *G05B 15/02* | (2006.01) |
| *G06F 3/04845* | (2022.01) |
| *H04N 17/00* | (2006.01) |

(Continued)

(52) U.S. Cl.
CPC ...... *A61B 1/00057* (2013.01); *A61B 1/00006* (2013.01); *G05B 15/02* (2013.01); *G06F 3/04845* (2013.01); *H04N 17/002* (2013.01); *A61B 1/00009* (2013.01);

(Continued)

(58) Field of Classification Search
CPC ............ A61B 1/00057; A61B 1/00006; A61B 1/00009; A61B 2017/00225; G05B 15/02; G06F 3/04845; G06F 3/04817; G06F 3/0482; H04N 17/002
See application file for complete search history.

(56) References Cited

U.S. PATENT DOCUMENTS

| | | | | |
|---|---|---|---|---|
| 4,345,211 A | * | 8/1982 | Longworth | ............. H03K 9/06 329/346 |
| 4,350,970 A | * | 9/1982 | von Tomkewitsch | ...................... G08G 1/096822 340/988 |

(Continued)

FOREIGN PATENT DOCUMENTS

| | | |
|---|---|---|
| JP | 2000-271065 A | 10/2000 |
| JP | 2002-45329 A | 2/2002 |

(Continued)

OTHER PUBLICATIONS

International Search Report dated Mar. 26, 2019 issued in PCT/JP2019/001326.

*Primary Examiner* — Nicholas Augustine
(74) *Attorney, Agent, or Firm* — Scully, Scott, Murphy & Presser, P.C.

(57) ABSTRACT

A central control apparatus that centrally controls a plurality of medical devices as controlled devices includes a processor. The processor is configured to: set a function allocated to one or more switches provided in the controlled devices, detect occurrence of an error of the controlled devices and a state of the occurred error, and change, based on a detection result of the error, the function allocated to the one or more switches to a function for restoration from the detected error.

20 Claims, 17 Drawing Sheets

(51) Int. Cl.
*A61B 17/00* (2006.01)
*G06F 3/04817* (2022.01)
*G06F 3/0482* (2013.01)

(52) U.S. Cl.
CPC ............ *A61B 2017/00225* (2013.01); *G06F 3/04817* (2013.01); *G06F 3/0482* (2013.01)

(56) References Cited

U.S. PATENT DOCUMENTS

| | | | | |
|---|---|---|---|---|
| 4,354,760 A * | 10/1982 | Schiffner | ............ | G01C 19/721 385/32 |
| 4,433,292 A * | 2/1984 | Frebault | ............ | H01J 29/98 324/404 |
| 4,518,184 A * | 5/1985 | Pecorini | ............ | B63B 21/54 114/221 R |
| 4,542,302 A * | 9/1985 | Griffioen | ............ | H05F 3/02 340/532 |
| 4,763,270 A * | 8/1988 | Itoh | ............ | G01C 21/3667 701/428 |
| 4,782,447 A * | 11/1988 | Ueno | ............ | G09B 29/106 701/431 |
| 4,821,211 A * | 4/1989 | Torres | ............ | G06F 40/10 345/902 |
| 4,827,252 A * | 5/1989 | Busbridge | ............ | G06T 15/04 345/441 |
| 4,899,285 A * | 2/1990 | Nakayama | ............ | G01S 19/49 701/472 |
| 5,101,425 A * | 3/1992 | Darland | ............ | H04Q 3/0087 379/112.01 |
| 5,257,023 A * | 10/1993 | Furuya | ............ | G08G 1/0969 340/995.13 |
| 5,297,253 A * | 3/1994 | Meisel | ............ | G06F 3/0482 707/E17.093 |
| 5,396,600 A * | 3/1995 | Thompson | ............ | G06F 9/451 705/28 |
| 5,463,605 A * | 10/1995 | Nishida | ............ | G11B 27/002 369/53.2 |
| 5,513,110 A * | 4/1996 | Fujita | ............ | G01C 21/3446 340/995.22 |
| 5,515,284 A * | 5/1996 | Abe | ............ | G01C 21/3881 73/178 R |
| 5,546,311 A * | 8/1996 | Sekine | ............ | G08G 1/0965 340/902 |
| 5,594,739 A * | 1/1997 | Lemieux | ............ | H04W 4/14 455/406 |
| 5,634,123 A * | 5/1997 | Bennion | ............ | G06F 12/023 |
| 5,673,872 A * | 10/1997 | Shimshi | ............ | B64C 39/001 244/62 |
| 5,699,486 A * | 12/1997 | Tullis | ............ | G06F 9/453 704/270.1 |
| 5,736,923 A * | 4/1998 | Saab | ............ | B61L 25/021 180/281 |
| 5,744,801 A * | 4/1998 | Diedrickson | ............ | G01J 5/34 250/342 |
| 5,751,228 A * | 5/1998 | Kamiya | ............ | G08G 1/0969 73/178 R |
| 5,835,905 A * | 11/1998 | Pirolli | ............ | G06F 16/35 707/999.005 |
| 5,864,819 A * | 1/1999 | De Armas | ............ | G06F 8/38 704/E15.044 |
| 5,958,012 A * | 9/1999 | Battat | ............ | G06F 3/04817 709/224 |
| 6,002,398 A * | 12/1999 | Wilson | ............ | G06F 3/0483 715/777 |
| 6,002,403 A * | 12/1999 | Sugiyama | ............ | G06F 3/0482 715/848 |
| 6,002,946 A * | 12/1999 | Reber | ............ | G06K 7/10881 398/1 |
| 6,047,320 A * | 4/2000 | Tezuka | ............ | H04L 41/00 714/21 |
| 6,056,248 A * | 5/2000 | Ma | ............ | G06F 1/1601 248/920 |
| 6,061,003 A * | 5/2000 | Harada | ............ | G01C 21/367 701/450 |
| 6,081,609 A * | 6/2000 | Narioka | ............ | G01C 21/26 382/113 |
| 6,185,574 B1* | 2/2001 | Howard | ............ | G06F 16/188 707/999.102 |
| 6,185,589 B1* | 2/2001 | Votipka | ............ | G06F 40/177 715/768 |
| 6,219,034 B1* | 4/2001 | Elbing | ............ | G06F 3/03543 345/158 |
| 6,263,507 B1* | 7/2001 | Ahmad | ............ | G06F 16/7834 725/38 |
| 6,266,682 B1* | 7/2001 | LaMarca | ............ | G06F 16/93 707/999.005 |
| 6,289,380 B1* | 9/2001 | Battat | ............ | H04L 41/069 709/224 |
| 6,329,994 B1* | 12/2001 | Gever | ............ | G06T 13/20 345/620 |
| 6,331,861 B1* | 12/2001 | Gever | ............ | G06T 13/20 345/626 |
| 6,381,579 B1* | 4/2002 | Gervais | ............ | G06Q 10/06311 707/999.009 |
| 6,496,837 B1* | 12/2002 | Howard | ............ | G06F 16/168 707/999.102 |
| 6,519,612 B1* | 2/2003 | Howard | ............ | G06F 16/192 707/999.102 |
| 6,562,076 B2* | 5/2003 | Edwards | ............ | G06F 40/10 715/229 |
| 6,934,749 B1* | 8/2005 | Black | ............ | H04L 69/18 709/224 |
| 7,028,306 B2* | 4/2006 | Boloker | ............ | G06F 8/38 719/310 |
| 7,117,432 B1* | 10/2006 | Shanahan | ............ | G06F 16/353 715/236 |
| 2002/0016620 A1 | 2/2002 | Tsujita | | |
| 2004/0113938 A1* | 6/2004 | Akerfeldt | ............ | G06F 16/258 715/738 |
| 2005/0071749 A1* | 3/2005 | Goerke | ............ | G06F 8/38 715/205 |
| 2005/0076311 A1* | 4/2005 | Kusterer | ............ | G06F 3/0481 715/853 |
| 2006/0173240 A1 | 8/2006 | Fukuyama et al. | | |
| 2012/0036442 A1* | 2/2012 | Dare | ............ | G06F 8/60 715/736 |
| 2012/0036552 A1* | 2/2012 | Dare | ............ | H04L 41/0803 726/1 |
| 2013/0246135 A1* | 9/2013 | Wang | ............ | G06F 17/00 701/2 |
| 2017/0017815 A1* | 1/2017 | Caso | ............ | G06F 21/35 |
| 2018/0263715 A1 | 9/2018 | Maeda et al. | | |
| 2019/0206563 A1* | 7/2019 | Shelton, IV | ............ | A61B 34/20 |
| 2020/0176095 A1* | 6/2020 | Ansari | ............ | H04L 63/083 |

FOREIGN PATENT DOCUMENTS

| | | |
|---|---|---|
| JP | 2003-044128 A | 2/2003 |
| JP | 2004-041401 A | 2/2004 |
| JP | 3576466 B2 | 10/2004 |
| JP | 2006-091343 A | 4/2006 |
| JP | 2006-187427 A | 7/2006 |
| JP | 2006-325940 A | 12/2006 |
| JP | 2008-161569 A | 7/2008 |
| JP | 2011-55988 A | 3/2011 |
| JP | 2012-040169 A | 3/2012 |

* cited by examiner

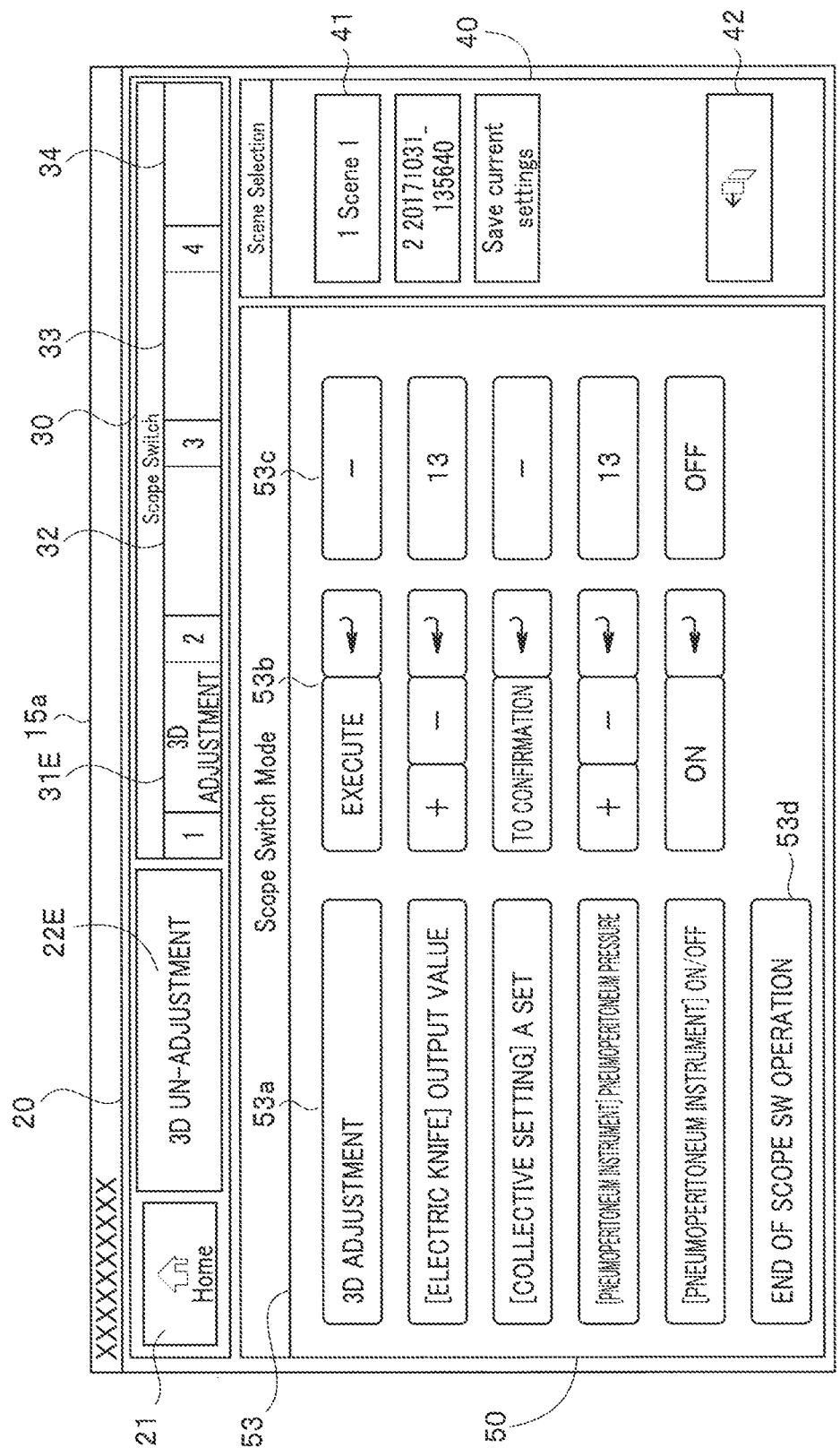

CENTRAL CONTROL APPARATUS, CENTRAL CONTROL SYSTEM, AND CONTROL METHOD FOR CONTROLLED DEVICES

CROSS REFERENCE TO RELATED APPLICATION

This application is a continuation application of PCT/JP2019/001326 filed on Jan. 17, 2019, the entire contents of which are incorporated herein by this reference.

BACKGROUND OF THE INVENTION

1. Field of the Invention

The present invention relates to a central control apparatus, a central control system, and a control method for controlled devices, capable of performing remote control of medical devices.

2. Description of the Related Art

There has been proposed a medical system adopting a system controller that controls medical devices such as an endoscope used in a surgical operation. In an operation room, there are various devices such as an endoscope, a video processor, an electric knife, a pneumoperitoneum apparatus, a recording apparatus, and a display, which are medical devices. These devices can be individually operated. However, it is annoying for a surgeon and a nurse to move to positions of the respective devices and operate the respective devices during a surgical operation. Therefore, a system controller that collectively operates the devices in the operation room is adopted.

The system controller includes an operation panel for centrally operating the respective medical devices. On the operation panel of the system controller, individual operation screens for respective devices, an operation screen for collectively operating a plurality of devices, and the like can be displayed. A user can perform operation and setting for respective devices in the operation room using the operation screens of the system controller.

For example, it is possible to allocate, with the system controller, functions to scope switches provided in the endoscope. The system controller can cause the operation panel to display a menu display for the allocation of the functions of the scope switches. The user is capable of allocating the functions to the scope switches by touching the operation panel.

Japanese Patent Application Laid-Open Publication No. 2003-44128 discloses a technique for, in a central control apparatus, displaying a help image for trouble shooting when a trouble of a controlled device occurs. Japanese Patent Application Laid-Open Publication No. 2006-91343 discloses an image processing apparatus having a browser display function, the image processing apparatus performing optimum error notification control corresponding to a state of use of an operation panel.

SUMMARY OF THE INVENTION

A central control apparatus according to an aspect of the present invention is a central control apparatus that centrally controls a plurality of medical devices as controlled devices. The central control apparatus includes a processor, the processor being configured to: set a function allocated to one or more switches provided in the controlled devices; detect occurrence of an error of the controlled devices and a state of the occurred error; and change, based on a detection result of the error, the function allocated to the one or more switches to a function for restoration from the detected error.

A central control system according to an aspect of the present invention includes: an endoscope; and a central control apparatus that centrally controls a plurality of medical devices as controlled devices. The central control apparatus includes a processor, the processor being configured to: set a function allocated to one or more switches provided in the controlled devices; detect occurrence of an error of the controlled devices and a state of the occurred error; and change, based on a detection result of the error, the function allocated to the one or more switches to a function for restoration from the detected error.

A control method for controlled devices according to an aspect of the present invention is a method for controlling a plurality of medical devices as controlled devices. The control method including: setting a function allocated to one or more switches provided in the controlled devices; detecting occurrence of an error of the controlled devices and a state of the occurred error; and changing, based on a detection result of the error, the function allocated to the one or more switches to a function for restoration from the detected error.

BRIEF DESCRIPTION OF THE DRAWINGS

FIG. 17 is an explanatory diagram showing an example of a setting screen at error occurrence time.

DETAILED DESCRIPTION OF THE PREFERRED EMBODIMENT(S)

Embodiments of the present invention are explained in detail below with reference to the drawings.

First Embodiment

A system controller, which is a central control apparatus, centrally operates, for example, various medical devices disposed in an operation room and can control allocation of functions to scope switches of an endoscope. In the present embodiment, the system controller is configured to, at error occurrence time, automatically change the functions allocated to the scope switches and automatically reset the functions allocated to the scope switches at restoration time from an error. Consequently, the system controller enables the scope switches to be utilized even at the error occurrence time and allocates functions necessary for the restoration from the error to the scope switches to make it possible to quickly perform the restoration from the error.

Figure 1:
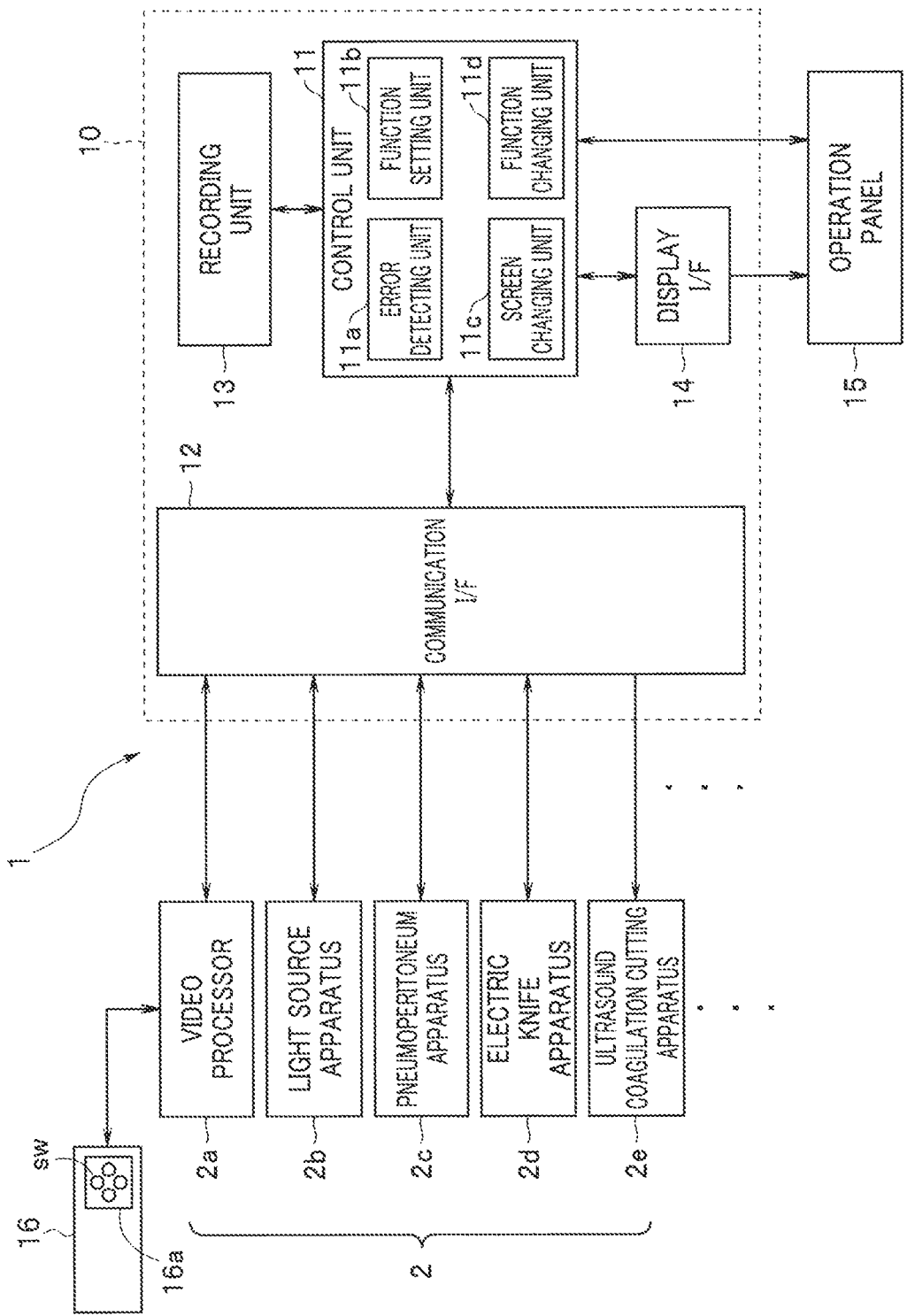
FIG. 1 is a block diagram showing a central control system including a central control apparatus of the present invention.

FIG. 1 is a block diagram showing a central control system including a central control apparatus of the present invention.

A central control system 1 in the present embodiment includes, as shown in FIG. 1, controlled devices 2 configured by a plurality of medical devices and a system controller 10, which is a central control apparatus. In FIG. 1, as the controlled devices 2, a video processor 2a, a light source apparatus 2b, a pneumoperitoneum apparatus 2c, an electric knife apparatus 2d, an ultrasound coagulation cutting apparatus 2e are illustrated. However, other various devices that can be disposed in an operation room or the like can be adopted. In the system controller 10, an operation panel 15 that receives operation by an operator such as a nurse is provided. Note that an endoscope 16 is connected to the video processor 2a.

The endoscope 16 includes a not-shown elongated insertion section. The endoscope 16 is driven by the video processor 2a, picks up an image of a subject with an image sensor such as a CCD or CMOS sensor provided at a distal end of the insertion section, and outputs an image pickup signal to the video processor 2a. The video processor 2a is configured to apply predetermined signal processing to the image pickup signal inputted from the endoscope 16 to be able to generate an endoscopic image and cause a not-shown monitor to display the endoscopic image.

In the endoscope 16, an operation section is provided on a proximal end side of the insertion section. In the operation section, a scope switch group 16a configured by a plurality of scope switches sw is provided. Note that, in FIG. 1, an example is shown in which four scope switches sw are provided. However, the number of scope switches sw is not limited to four. Switch IDs for identifying the respective scope switches sw are allocated to the respective scope switches sw. The endoscope 16 is configured to, when a user operates any one of the scope switches sw, transmit information concerning a switch ID for identifying the operated scope switch sw to the system controller 10 via the video processor 2a.

The system controller 10 includes a communication I/F 12 for performing communication with the respective controlled devices 2. The communication I/F 12 is capable of transmitting signals by serial communication such as RS-232C or an infrared ray. The communication I/F 12 can transmit, to the controlled devices 2, signals for respectively driving the respective controlled devices 2 from the control unit 11.

The system controller 10 includes a control unit 11. The control unit 11 may be configured by a processor using a CPU or an FPGA or may operate according to a program stored in a not-shown memory and control respective units or may realize a part or all of functions with a hardware electronic circuit. The control unit 11 controls operation of the entire system controller 10.

The control unit 11 is configured to be able to control a display I/F 14 to display, on a display screen of the operation panel 15, an operation display for receiving GUI (graphical user interface) operation of the user. Note that display data for displaying the operation display is stored in a recording unit 13. The display data stored in the recording unit 13 is given to the display I/F 14 from the control unit 11. The display I/F 14 generates the display data for the operation display according to the control by the control unit 11 and gives the display data to the operation panel 15.

The operation panel 15 is controlled by the control unit 11 and displays the operation display given from the display I/F 14 on the display screen. A not-shown touch panel is provided on the display screen of the operation panel 15. When an operator, for example, touches respective display portions of the operation display via the touch panel, the operation panel 15 generates operation signals corresponding to GUI operation on the respective display portions and outputs the operation signals to the control unit 11. The control unit 11 generates, based on the operation signals from the operation panel 15, control signals for controlling the controlled devices 2 and outputs the control signals to the corresponding controlled devices 2 via the communication I/F 12.

In this way, the control unit 11 is configured to be able to centrally operate the controlled devices 2 such as the video processor 2a, the light source apparatus 2b, the pneumoperitoneum apparatus 2c, the electric knife apparatus 2d, and the ultrasound coagulation cutting apparatus 2e. The control unit 11 is configured to be able to, when communication is performed between the system controller 10 and these apparatuses, display setting states of the connected apparatuses and a setting screen for an operation switch and the like on the display screen of the operation panel 15. Note that the operation panel 15 is configured such that an operation input such as a change of a setting value can be performed by operation of the touch panel.

The control unit 11 can also acquire operation information indicating operation states of the respective controlled devices 2 via the communication I/F 12 and change the operation display on the operation panel 15 to a display reflecting the operation information and cause the operation panel 15 to display the display. For example, the control unit 11 is configured to be able to cause the operation panel 15 to display, as the operation display, a device selection display for selecting which peripheral devices are operated as the controlled devices 2, a display for operating the selected controlled devices 2, and the like.

Further, the control unit 11 can cause the operation panel 15 to display, as the operation display, on the display screen of the operation panel 15, a setting display for allocating functions to the scope switches sw of the endoscope 16 and indicating a state of the allocation.

The control unit 11 is configured to create display data of the operation display based on setting information recorded in the recording unit 13. In the recording unit 13, error time setting information, which is setting information when an error occurs, is recorded besides normal time setting information, which is setting information in a normal state in which an error does not occur.

A function setting unit 11b is provided in the control unit 11 for allocation of functions to the scope switches sw. The function setting unit 11b is configured to set, based on operation of the operation panel 15 by the user, functions allocated to the respective scope switches sw and record the setting information (the normal time setting information) in the recording unit 13. For example, the function setting unit 11b registers, in the normal time setting information, correspondence between respective switch IDs respectively allocated to the respective scope switches sw and the respective functions. Note that, in the normal time setting information, setting for each of stages of control of the respective controlled devices 2 can be registered for each of the respective controlled devices 2.

The control unit 11 is configured to, when a switch ID is inputted by operation of the scope switch sw of the endoscope 16, read out a function designated by the switch ID and control the respective units in order to realize the function.

In the present embodiment, the control unit 11 includes an error detecting unit 11a. The error detecting unit 11a detects whether an error occurs in the controlled device 2 and a state of the occurred error. The error that occurs in the controlled device 2 can be detected according to transmitting and receiving of various signals with the controlled device 2 via the communication I/F 12. The error detecting unit 11a is configured to, when detecting that an error occurs in the controlled device 2, a state of the occurred error, and restoration from the error, output a detection result to a screen changing unit 11c and a function changing unit 11d.

The screen changing unit 11c is configured to, at error occurrence time of the controlled device 2, automatically change an operation display in a normal state (a normal time operation display) according to an error state and display an error time operation display. The screen changing unit 11c is configured to, when the controlled device 2 is restored from the error, automatically return the error time operation display to the normal time operation display. Note that the screen changing unit 11c performs display of the normal time operation display and the error time operation display based on the normal time setting information and the error time setting information recorded in the recording unit 13.

In the present embodiment, at error occurrence time of the controlled device 2, the function changing unit 11d is configured to automatically change, according to an error state, functions at the normal state time allocated to the scope switches sw (hereinafter referred to as normal time allocated functions) and change the allocation to functions corresponding to the error state (hereinafter referred to as error time allocated functions). The function changing unit 11d is configured to, when the controlled device 2 is restored from the error, automatically return the functions allocated to the scope switches sw to the normal time allocated functions. Note that, in the error time setting information recorded in the recording unit 13, setting is registered for each of error states. The function changing unit 11d performs setting of the error time allocated functions based on the error time setting information recorded in the recording unit 13.

Figure 2:
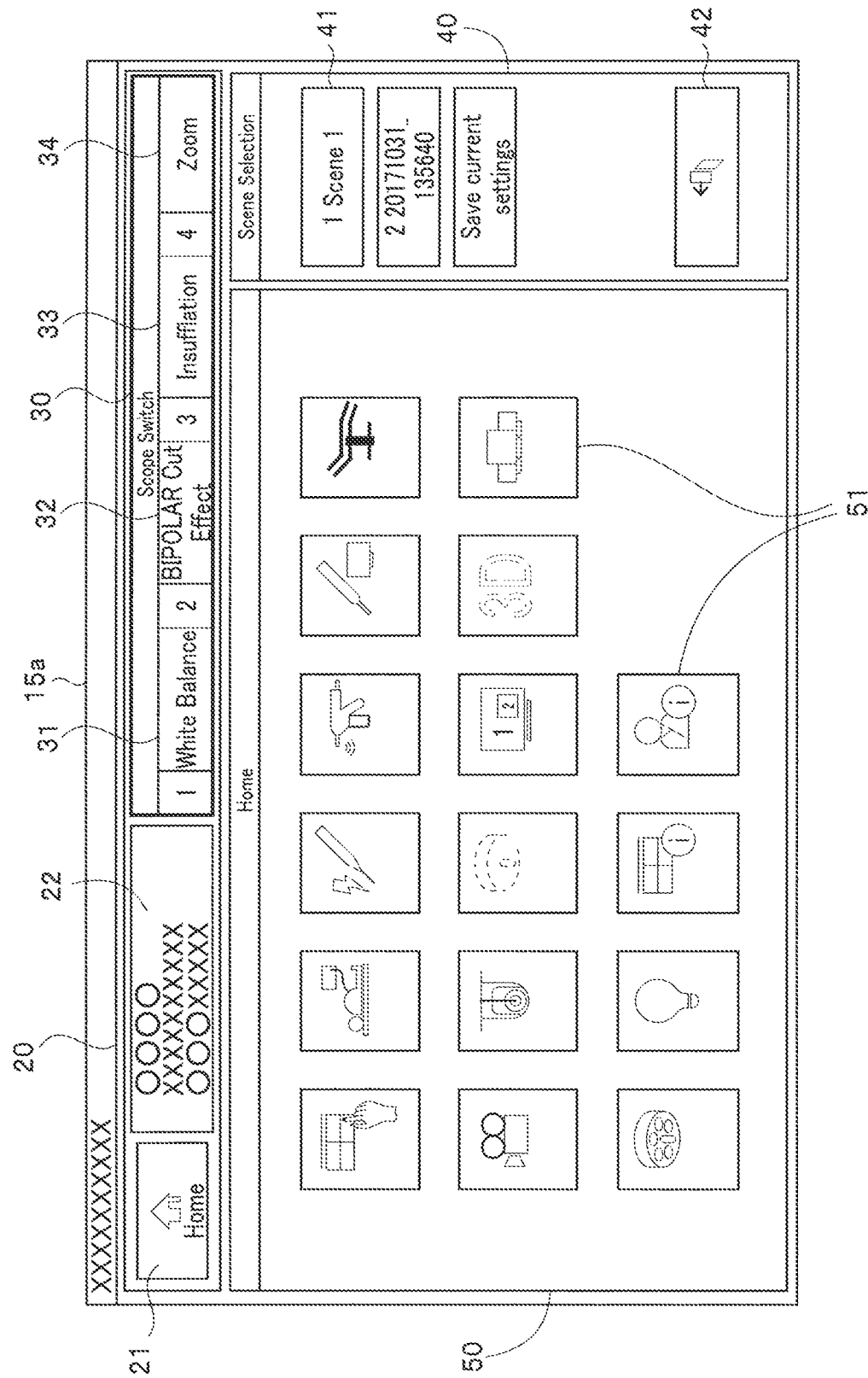
FIG. 2 is an explanatory diagram showing an example of an operation display displayed based on setting information stored in a recording unit 13.
Figure 3:
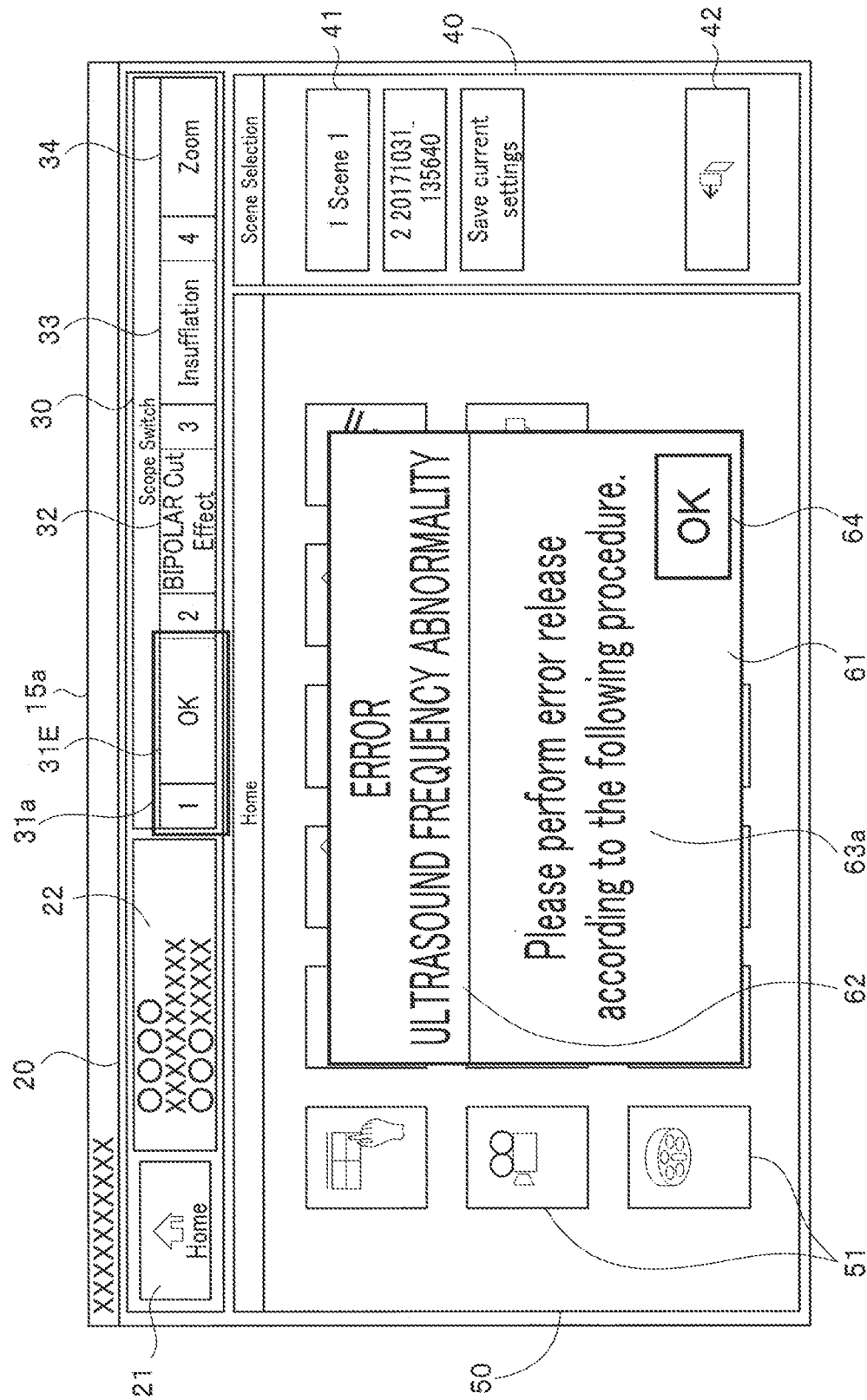
FIG. 3 is an explanatory diagram showing a display example at error occurrence time.
Figure 4:
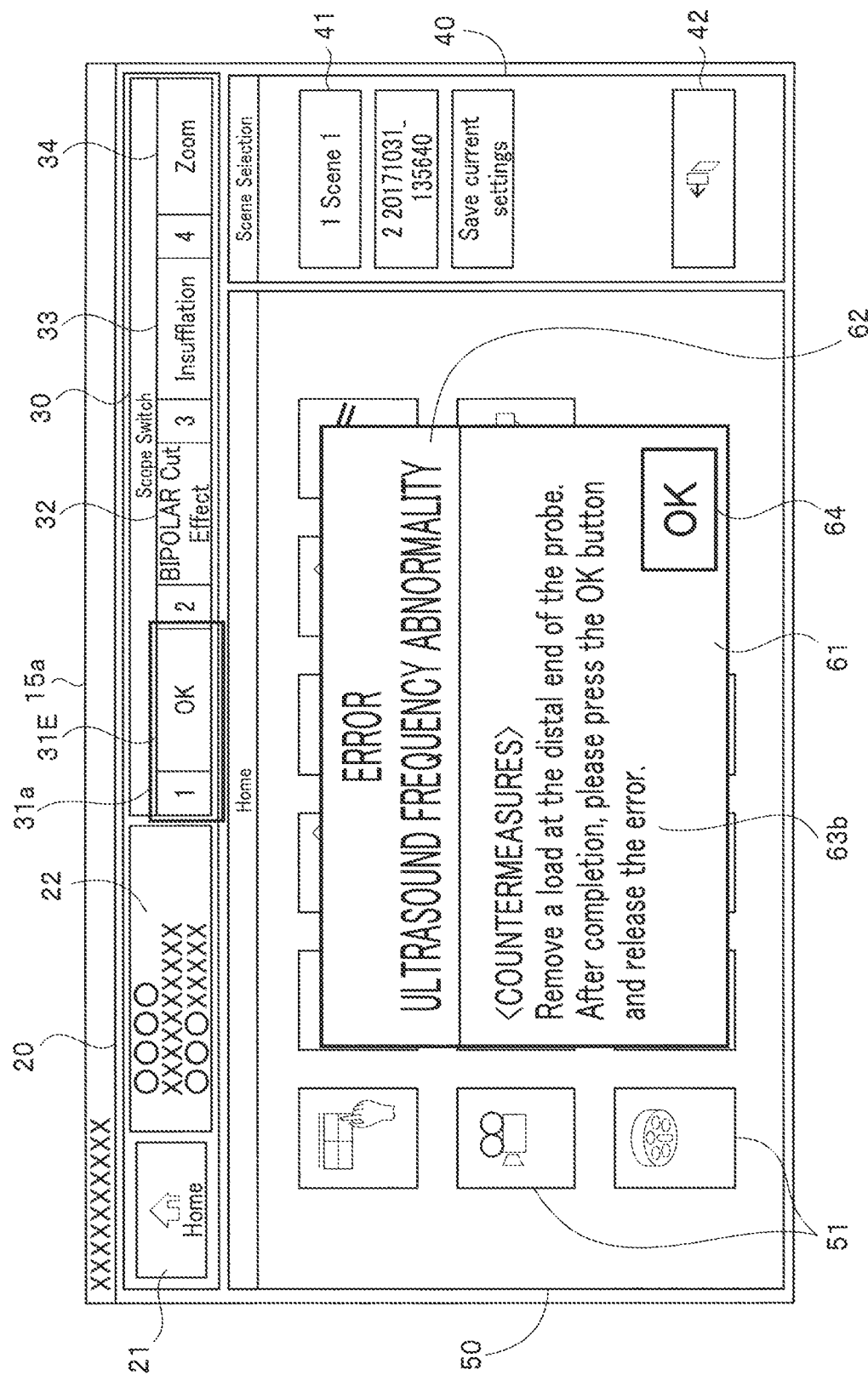
FIG. 4 is an explanatory diagram showing a display example in the case in which an error countermeasure is performed.
Figure 5:
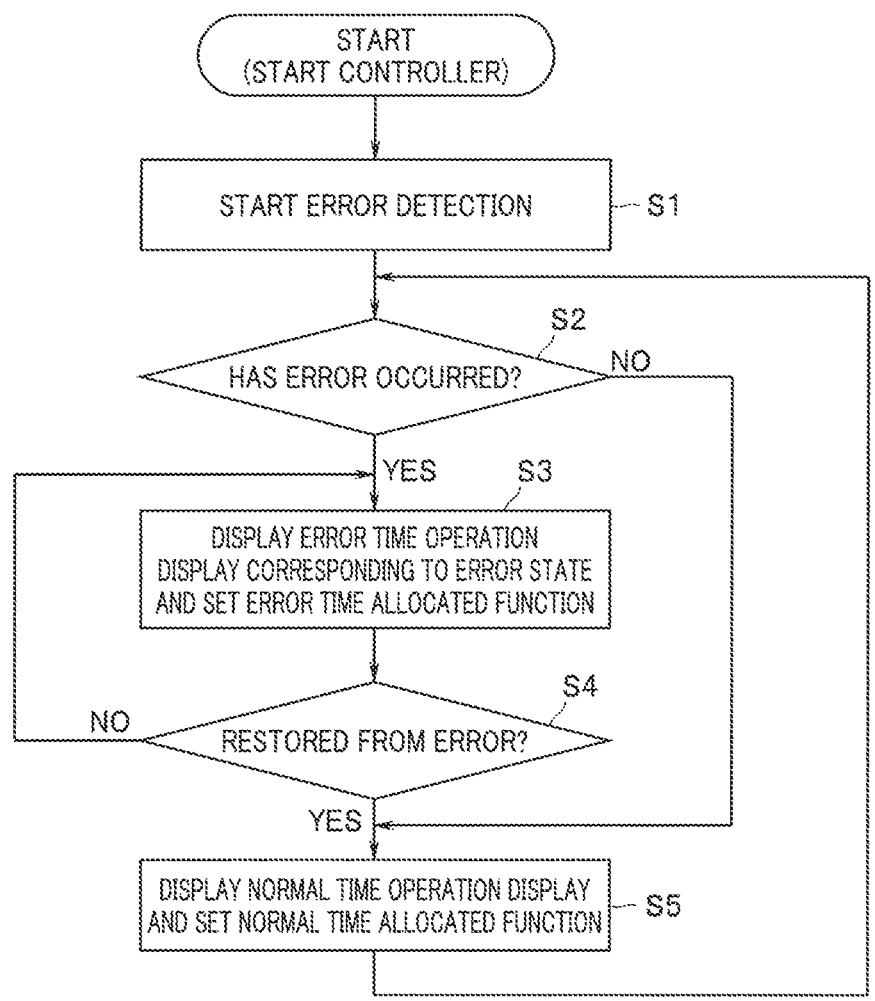
FIG. 5 is a flowchart for explaining control by a control unit 11.

Subsequently, operation in the embodiment configured as explained above is explained with reference to FIG. 2 to FIG. 5. FIG. 2 is an explanatory diagram showing an example of an operation display displayed based on the setting information stored in the recording unit 13. The operation display shown in FIG. 2 indicates an example of a home screen for central control in the central control system. FIG. 3 is an explanatory diagram showing a display example at error occurrence time. FIG. 4 is an explanatory diagram showing a display example in the case in which an error countermeasure is performed. FIG. 5 is a flowchart for explaining control by the control unit 11.

When a power supply of the system controller 10 is turned on, the error detecting unit 11a of the control unit 11 starts detection of an error that occurs in the controlled devices 2 (step S1 in FIG. 5) and determines presence or absence of an error (step S2). When a detection result of the error detecting unit 11a indicates that an error has not occurred, the control unit 11 performs the normal time operation display and sets the normal time allocated functions (step S5).

In other words, the control unit 11 reads out display data of the normal time operation display from the recording unit 13 and gives the display data to the display I/F 14. The display I/F 14 generates the normal time operation display based on the display data and gives the normal time operation display to the operation panel 15. In this way, a home screen (an initial screen), which is the normal time operation display, is displayed on the display screen of the operation panel 15.

Note that, in the recording unit 13, the normal time setting information, in which the normal time allocated functions allocated to the scope switches sw are registered, is recorded by the function setting unit 11b. When the scope switch sw is operated, the control unit 11 controls the respective units to execute the normal time allocated function corresponding to a switch ID transmitted from the endoscope 16.

FIG. 2 shows a display example of the home screen, which is the normal time operation display. The home screen displayed on a display screen 15a of the operation panel 15 includes an upper side display region 20 and a right side display region 40 always displayed in a logon state of the system controller 10 and includes a center display region 50 in which a display changes according to a selected menu.

In the upper side display region 20, a home button 21 for instructing transition to the home screen, a display 22 showing a surgeon, a procedure, date and time, and the like, and a scope switch display 30 showing functions allocated to the respective scope switches sw of the scope switch group 16a provided in the endoscope 16 are displayed. In the example shown in FIG. 2, the scope switch display 30 shows functions allocated to four scope switches sw of the endoscope 16.

In the right side display region 40, a procedure selection button group 41 for selecting respective scenes of the procedure and an end button 42 for executing end processing are displayed. In the example shown in FIG. 2, an example is shown in which two selection buttons are displayed as the procedure selection button group 41.

In the center display region 50, an item to be displayed changes according to a selected menu. In the home screen shown in FIG. 2, icons 51 for selecting devices of the controlled devices 2 are displayed in the center display region 50. When a predetermined icon 51 is, for example, touched, an operation display for operating a device allocated to the icon 51 is displayed.

The scope switch display 30 shown in FIG. 2 shows, with allocated displays 31 to 34, functions allocated to the respective scope switches sw by the function setting unit 11*b* at normal state time when an error has not occurred in the controlled devices 2. In other words, it is seen with the allocated display 31 that a white balance adjustment (White Balance) function is allocated to a scope switch with a scope ID "1" (hereinafter referred to as scope switch sw1). It is seen with the allocated display 32 that a switching (BIPOLAR Cut Effect) function of an effect mode of a bipolar electric knife is allocated to a scope switch with a scope ID "2" (hereinafter referred to as scope switch sw2). It is seen with the allocated display 33 that an operation start and end operation (Insufflation) function of a pneumoperitoneum apparatus is allocated to a scope switch with a scope ID "3" (hereinafter referred to as scope switch sw3). It is seen with the allocated display 34 that a zoom operation (Zoom) function of an operation field camera or the like disposed in an operation room is allocated to a scope switch with a scope ID "4" (hereinafter referred to as scope switch sw4).

Therefore, for example, when the scope switch sw1 is operated at the normal state time, the control unit 11 determines referring to the normal time setting information that white balance adjustment is instructed and performs control for the white balance adjustment.

At the normal state time, a nurse or the like performs central operation on the controlled devices 2 using the operation panel 15. The control unit 11 transmits and receives data to and from the controlled devices 2 via the communication I/F 12 and drives the controlled devices 2 based on operation of the operation panel 15. The control unit 11 acquires information concerning states of the controlled devices 2. The control unit 11 generates, based on the information acquired from the recording unit 13 and the controlled devices 2, data of an operation display displayed on the display screen 15*a* of the operation panel 15 and gives the data to the display I/F 14. The display I/F 14 is controlled by the control unit 11 to generate an operation display and give the operation display to the operation panel 15. In this way, the operation display corresponding to the operation of the operation panel 15 and the state of the controlled devices 2 is displayed on the operation panel 15.

It is assumed that an error occurs in the controlled device 2. Then, the error is detected by the error detecting unit 11*a* (step S2) and a detection result is given to the screen changing unit 11*c* and the function changing unit 11*d*. The screen changing unit 11*c* causes the operation panel 15 to display the error time operation display corresponding to an error state and the function changing unit 11*d* sets the error time allocated functions corresponding to the error state (step S3). In other words, the screen changing unit 11*c* generates, referring to the error time setting information based on the detection result of the error, display data for causing the operation panel 15 to display the error time operation display corresponding to the state of the error and outputs the display data to the operation panel 15 via the display I/F 14. In this way, the error time operation display is displayed on the display screen 15*a* of the operation panel 15.

FIG. 3 shows an example of the error time operation display in this case. The example shown in FIG. 3 shows the error time operation display in which an error display 61 is displayed in the center of the center display region 50. Note that FIG. 3 is an example in which an error occurs in a state of the home screen. The icons 51 are displayed on the center display region 50. At error occurrence time, in a state of display in the center display region 50 at timing when the error occurs, the error display 61 is displayed over the display. The error display 61 shown in FIG. 3 includes an error content display 62 indicating that an abnormality has occurred in an ultrasound frequency of the ultrasound coagulation cutting apparatus 2*e*.

The error display 61 includes a guide display 63*a* for supporting restoration operation from the error. A message "Please perform error release according to the following procedure" is displayed in the guide display 63*a* to support operation that the user should perform next. An OK display 64 is included in the error display 61. The screen changing unit 11*c* is configured to continue to display the error display 61 shown in FIG. 3 until the user performs operation on the OK display 64. In other words, for restoration from the error, the user needs to perform operation on the OK display 64.

However, the operation panel 15 is present in an unclean area. In order to touch the OK display 64, a doctor needs to request a nurse or the like to touch the OK display 64. Operation for restoration from an error is annoying. Therefore, in the present embodiment, the function changing unit 11*d* is configured to, at error occurrence time, set the error time allocated functions in the scope switches sw. In other words, in the error time setting information, the error time allocated functions corresponding to an error state are registered. The function changing unit 11*d* reads out the error time setting information according to occurrence of an error to automatically change the functions allocated to the scope switches sw. According to this setting change, the screen changing unit 11*c* changes display of the scope switch display 30.

In the example shown in FIG. 3, an allocated display 31E is displayed instead of the allocated display 31 shown in FIG. 2. Note that, in the following explanation, E is added to signs in a display at error time different from a display at normal time in the operation display. The allocated display 31E indicates that an operation function of an OK button is allocated to the scope switch sw1. At error time, a highlighted display 31*a* is displayed such that the display of the allocated display 31E is conspicuous. For example, the highlighted display 31*a* is a display more easily recognized by the user with a color different from other portions, brighter display, flashing, or the like.

When a surgeon operates the scope switch sw1 in this state, the control unit 11 determines with the error time setting information that the error time allocated function allocated to the scope switch sw1 is an operation function for the OK button and performs the same processing as processing performed when the OK button is touched. In other words, in this case, the control unit 11 determines that the user grasps content of the guide display 63*a*. The screen changing unit 11*c* updates the error display 61 and causes the operation panel 15 to display a guide display 63*b* shown in FIG. 4. The guide display 63*b* shown in FIG. 4 is a display for supporting, with a message "<Countermeasures> Remove a load at the distal end of the probe. After completion, please press the OK button and release the error", operation that the user should perform next.

With the guide display 63*b*, the user can recognize operation necessary for restoration from the error, that is, removing the load at the distal end of the probe. The user can also recognize that the user needs to operate the OK display 64 after removing the load at the distal end of the probe. The user operates the scope switch sw1 again after removing the load at the distal end of the probe. As shown in FIG. 4, at this point in time as well, the operation function of the OK button is allocated to the scope switch sw1. With the operation of the scope switch sw1, it is possible to easily perform operation for restoration from the error.

The error detecting unit 11a continuously carries out error detection. When detecting restoration from the error with the error detection after the operation of the scope switch sw1 by the user (step S4), the error detecting unit 11a outputs a detection result to the screen changing unit 11c and the function changing unit 11d. The screen changing unit 11c causes the operation panel 15 to display the normal time operation display based on the normal time setting information and the function changing unit 11d sets the normal time allocated functions based on the normal time setting information (step S5). In this way, the normal time operation display displayed before the error occurrence is displayed on the display screen 15a of the operation panel 15. The functions allocated to the scope switches sw are returned to the functions at the normal state time.

In this way, in the present embodiment, when an error occurs in a controlled device set as a central control target, a function allocated to a scope switch is automatically changed to an error allocated function. When the controlled device is restored from the error, the function is automatically returned to a normal time allocated function. Consequently, even at error time, it is possible to utilize the scope switch. By allocating a function necessary for the restoration from the error to the scope switch, it is possible to quickly perform the restoration from the error. For example, by allocating a function of operating an operation panel to the scope switch, a doctor or the like is capable of operating, with the scope switch, the operation panel belonging to an unclean area. The doctor or the like performs panel operation necessary at restoration time from the error. Consequently, it is possible to quickly perform the restoration from the error. At error occurrence time, the normal time operation display displayed on the operation panel is automatically changed to the error time operation display. When the controlled device is restored from the error, the error time operation display is automatically returned to the normal time operation display. In the error time operation display, it is possible to perform operation support for the restoration from the error. It is possible to present the error time allocated function of the scope switch to the user. It is possible to efficiently support the restoration from the error.

Second Embodiment

Figure 6:
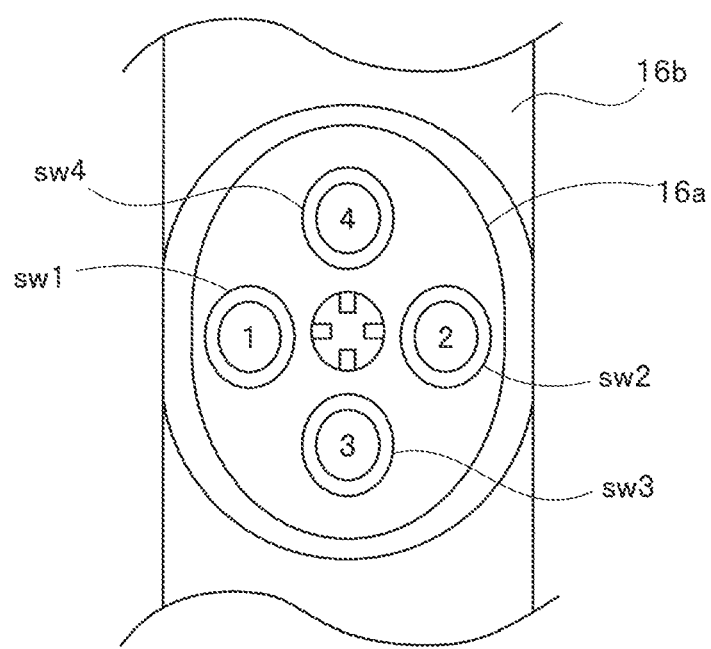
FIG. 6 is an explanatory diagram showing an example of an exterior of scope switches.
Figure 7:
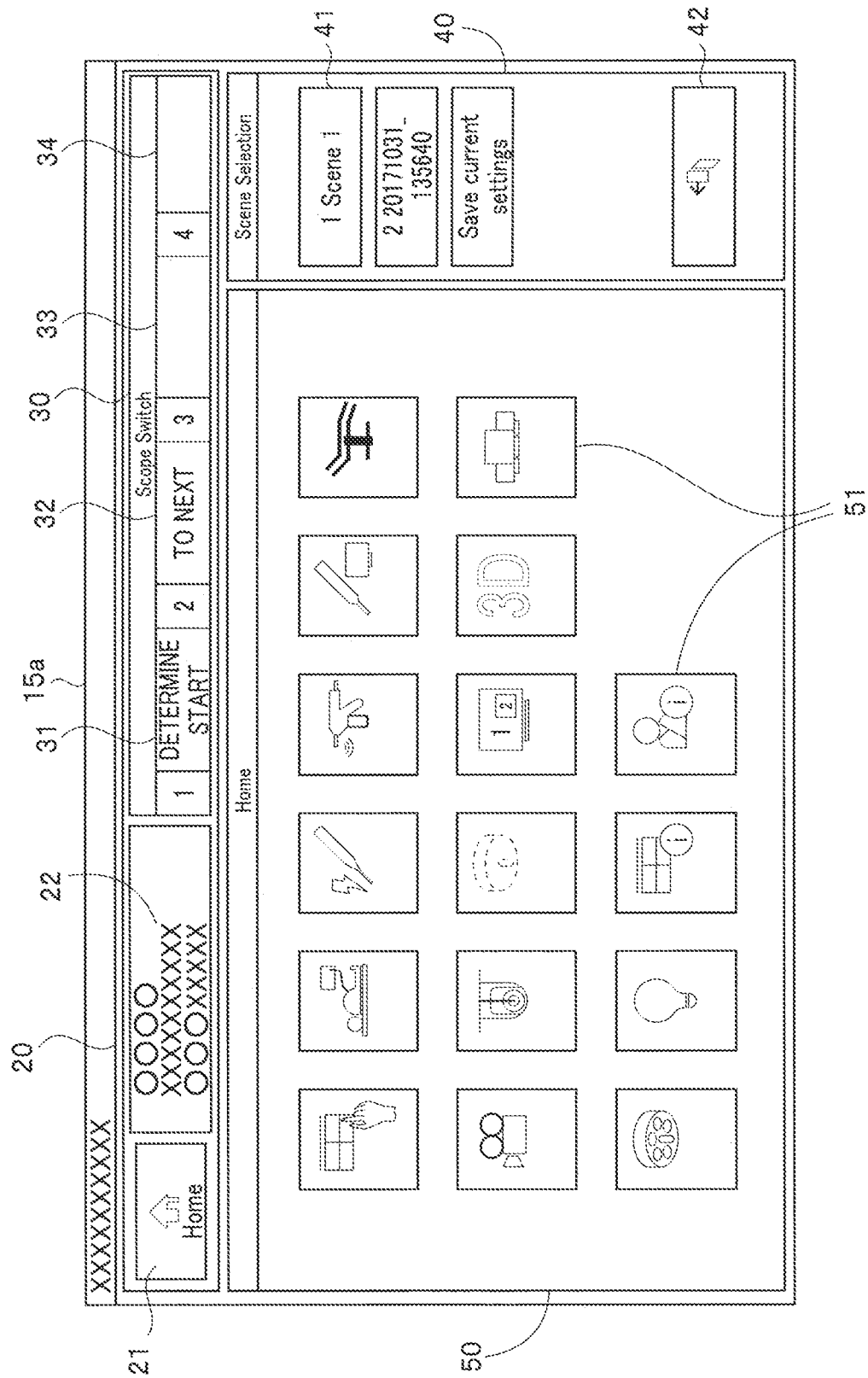
FIG. 7 is an explanatory diagram showing an example of a home screen.
Figure 8:
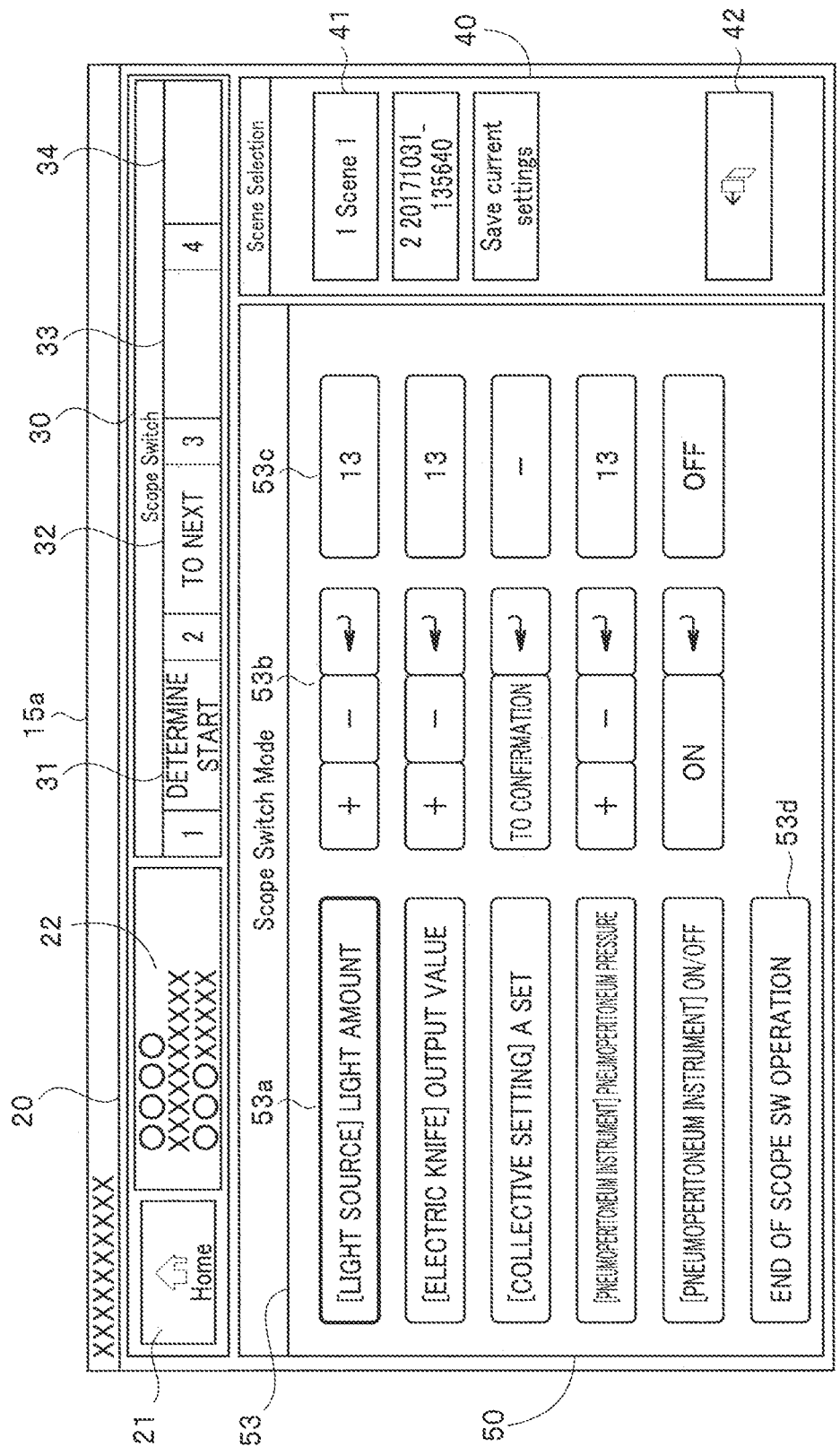
FIG. 8 is an explanatory diagram showing an example of a setting screen for various settings of controlled devices 2.
Figure 9:
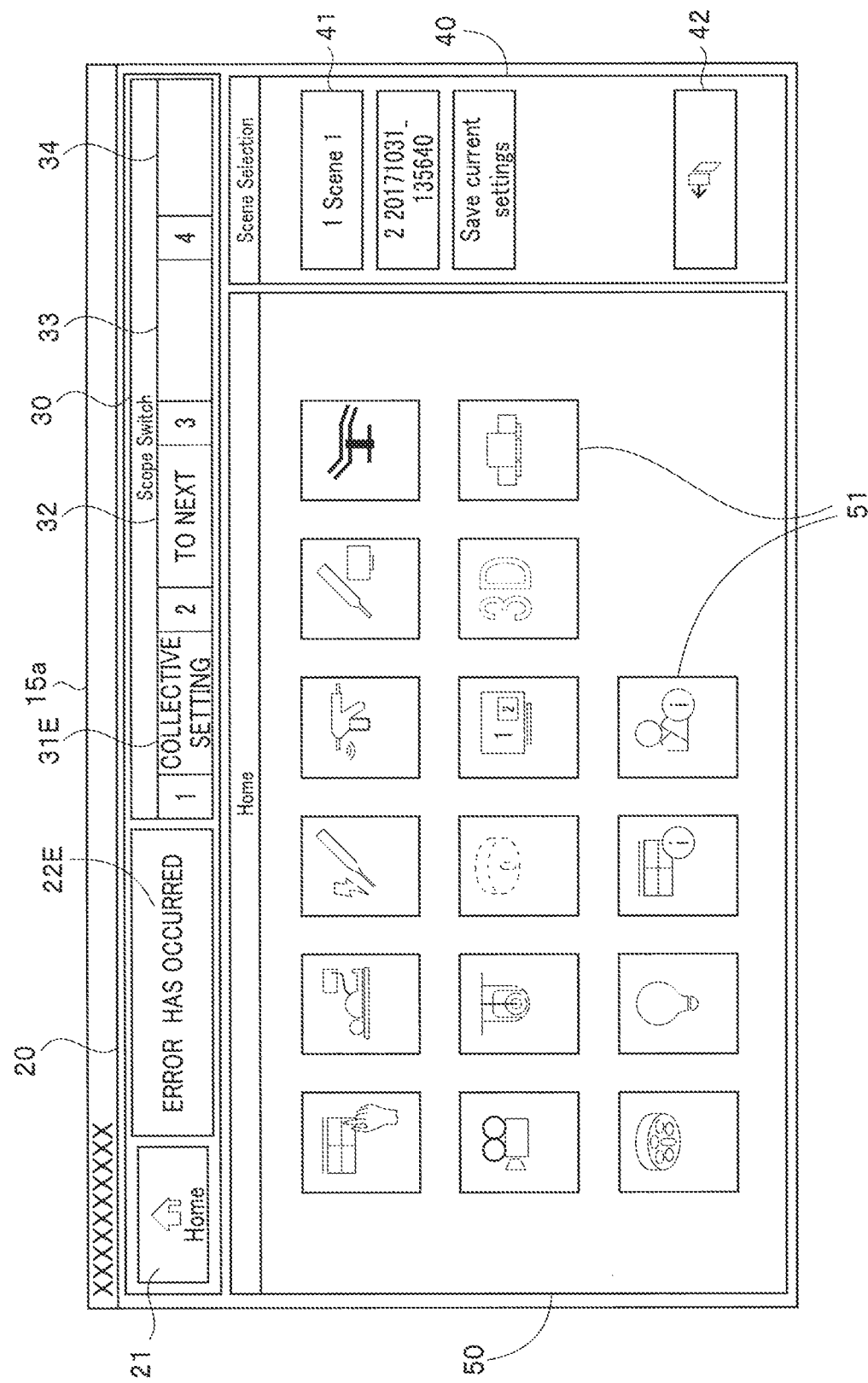
FIG. 9 is an explanatory diagram showing an example of a home screen at error occurrence time.
Figure 10:
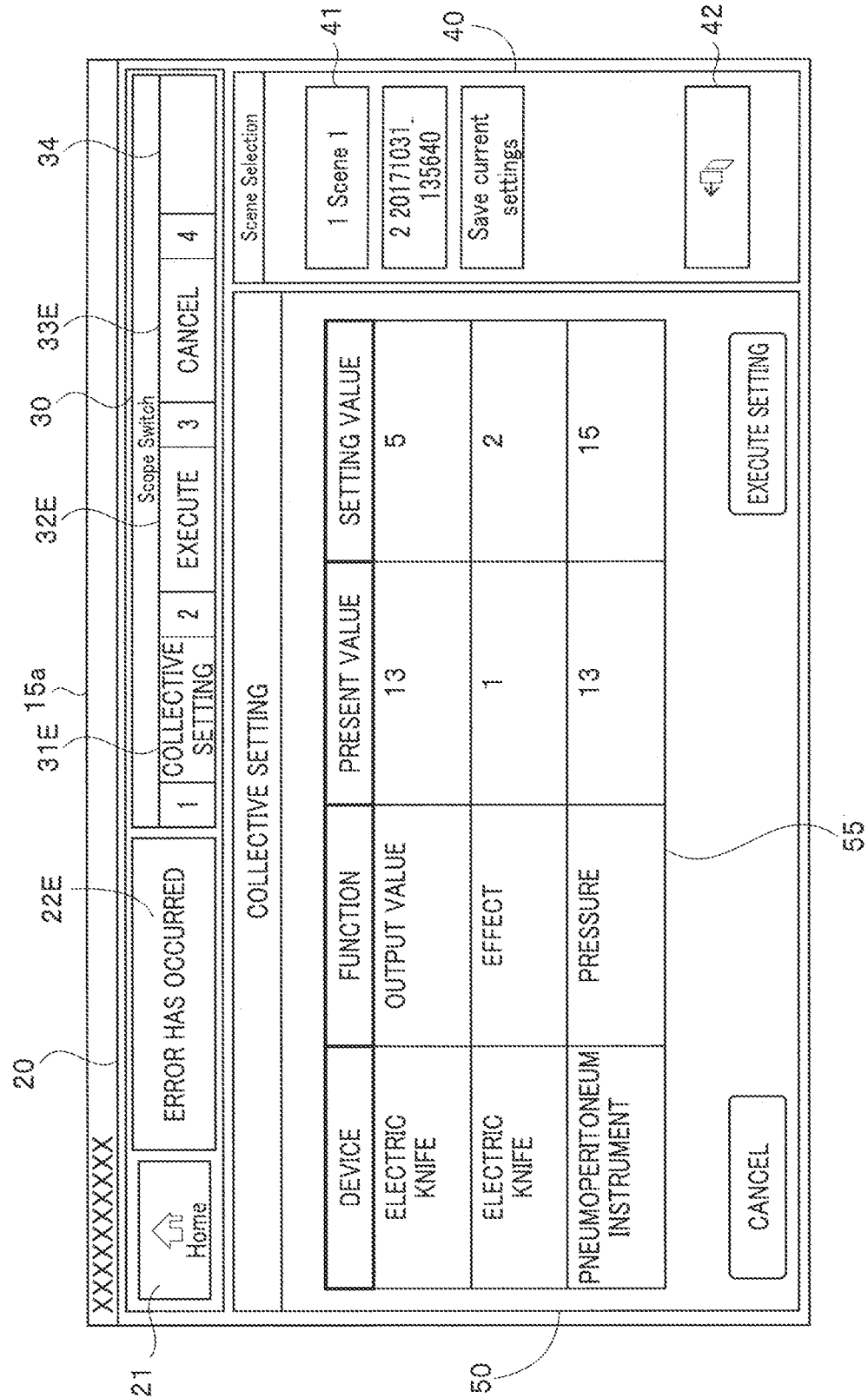
FIG. 10 is an explanatory diagram showing an example of a collective setting screen at error occurrence time.

FIG. 6 to FIG. 10 relate to a second embodiment of the present invention. FIG. 6 is an explanatory diagram showing an example of an exterior of scope switches. FIG. 7 is an explanatory diagram showing an example of a home screen. FIG. 8 is an explanatory diagram showing an example of a setting screen for various settings of the controlled devices 2. FIG. 9 is an explanatory diagram showing an example of a home screen at error occurrence time. FIG. 10 is an explanatory diagram showing an example of a collective setting screen at error occurrence time. A hardware configuration in the present embodiment is the same as the hardware configuration shown in FIG. 1. Explanation about the hardware configuration is omitted. The present embodiment indicates an operation display and allocated functions of the scope switches sw different from the operation display and the allocated functions in the first embodiment. The present embodiment enables collective setting for facilitating restoration from an error.

FIG. 6 shows an example of the scope switch group 16a provided in an operation section 16b of the endoscope 16. Four scope switches sw1 to sw4 are provided in the scope switch group 16a to surround a center of the operation section 16b. The scope switch sw1 and the scope switch sw2 are disposed in a direction perpendicular to a longitudinal direction of the operation section 16b. The scope switch sw3 and the scope switch sw4 are disposed in the longitudinal direction of the operation section 16b.

(Normal State Time)

For example, the function setting unit 11b allocates a start determining function for deciding a start and selection of setting to the scope switch sw1 and allocates the same moving (to next) function as a direction key to the scope switch sw2. FIG. 7 shows the same home screen as the home screen shown in FIG. 2. The example shown in FIG. 7 indicates that the start determining function is allocated to the scope switch sw1 and the moving (to next) function is allocated to the scope switch sw2 by the allocated displays 31 and 32.

It is assumed that the user operates the scope switch sw1 in a state in which the home screen shown in FIG. 7 is displayed. In this case, the screen changing unit 11c determines that display setting of the setting screen is designated by the user and transitions the display of the operation panel 15 to the setting screen shown in FIG. 8. The example shown in FIG. 8 indicates that a display of the center display region 50 is different from a display on the home screen and a setting display 53 adopting a mode operable by the scope switches sw (Scope Switch Mode) is displayed.

The setting display 53 includes five setting target displays 53a indicating setting targets, button displays 53b for changing settings, setting value displays 53c indicating setting values, and an end button display 53d for ending operation by the scope switches sw. The example shown in FIG. 8 indicates that setting of a light amount of a light source, setting of an output value of an electric knife, collective setting by an A set, setting of a pneumoperitoneum pressure of a pneumoperitoneum instrument, and ON/OFF setting of the pneumoperitoneum instrument are possible by the setting target displays 53a. The button displays 53b indicate an increase of a setting value with a + mark, indicate a decrease of a setting value with a − mark, and indicate movement of selection to an immediately upper layer with a return mark. In the button displays 53b, "To confirmation" corresponding to the collective setting by the A set indicates transition to a collective setting screen. ON and OFF corresponding to ON/OFF of the pneumoperitoneum instrument indicate that ON and OFF of the pneumoperitoneum instrument are possible. Present values of respective setting targets are indicated by the setting value displays 53c.

In FIG. 8, a thick frame indicates a currently selected display. For example, actually, a display being selected is indicated by a color, brightness, or the like different from other frames. In an initial state in which the display is transitioned to the setting screen shown in FIG. 8, for example, light amount setting for the light source is selected. When the scope switch sw2 is operated in a state in which any one of the setting target displays 53a or the end button display 53d is selected, a next display among the setting target displays 53a and the end button display 53d is selected. For example, when the scope switch sw2 is operated in a state in which the setting target display 53a of light amount setting for the light source is selected, the setting target display 53a of setting of an output value of the electric knife is selected.

When the scope switch sw1 is operated in a state in which any one of the setting target displays 53a is selected, the selection shifts to the button display 53b beside the setting target display 53a. When the scope switch sw2 is operated in a state in which any one of the button displays 53b is selected, for example, the button display 53b on the right side of the selected button display 53b is selected. When the scope switch sw2 is operated in a state in which the button display 53b at a most right end is selected, the button display 53b at a left end is selected. When the scope switch sw1 is operated in a state in which any one of the button displays 53b is selected, a determination operation corresponding to the selected button display 53b is performed. For example, the button display 53b with the plus mark increases a setting value and changes the setting value display 53c. The button display 53b with the minus mark reduces a setting value and changes the setting value display 53c. The button display 53b with the return mark returns a selected state to the setting target display 53a. Note that present setting values are always displayed in the setting value displays 53c.

In the case of the collective setting by the A set and the button display 53b of "To confirmation" is selected, a transition operation to the collective setting screen is performed by operation of the scope switch sw1. When the setting value display 53c corresponding to the setting target display 53a of ON and OFF of the pneumoperitoneum instrument is OFF and the button display 53b of ON is selected and the scope switch sw1 is operated, the pneumoperitoneum instrument changes to an ON operation, the setting value display 53c is switched from OFF to ON, and the button display 53b is switched from ON to OFF. Conversely, when the button display 53b of OFF is selected and the scope switch sw1 is operated, the pneumoperitoneum instrument changes to an OFF operation, the setting value display 53c is switched from ON to OFF, and the button display 53b is switched from OFF to ON. When the scope switch sw1 is operated in a state in which the end button display 53d is selected, the display setting transitions to the home screen shown in FIG. 7.

(Error Occurrence Time)

It is assumed that an error occurs in the controlled device 2. In this case, the function changing unit 11d changes the functions of the scope switches sw from the normal time allocated functions to the error time allocated functions. The screen changing unit 11c displays a display indicating that the error has occurred (error occurrence) as a display 22E in the upper side display region 20 and changes the scope switch display 30 to a display corresponding to the error time allocated functions.

FIG. 9 shows a display example in the case in which an error occurs at display time of the home screen shown in FIG. 7. The example shown in FIG. 9 indicates that, at error occurrence time, the collective setting function is set in the scope switch sw1 in the allocated display 31E. Note that when an error occurs at display time of the setting screen shown in FIG. 8, the center display region 50 is in a state of the setting display 53 in which the Scope Switch Mode is adopted, the display 22E changes to a display indicating the error occurrence, and the allocated display 31E changes to a display indicating that the collective setting function is set in the scope switch sw1. At error occurrence time, a user such as a doctor is capable of easily displaying the collective setting screen by operating the scope switch sw1.

FIG. 10 shows the collective setting screen displayed on the operation panel 15 in this case. The collective setting screen is an operation display for collectively performing various settings for restoring the controlled devices 2 to the normal state from an error in a short time. The function changing unit 11d allocates an execution function to the scope switch sw2 and allocates a cancel function to the scope switch sw3. The screen changing unit 11c indicates that the execution function is allocated to the scope switch sw2 by the allocated display 32E and the cancel function is allocated to the scope switch sw3 by the allocated display 33E as shown in FIG. 10.

The screen changing unit 11c displays the collective setting display 55 in the center display region 50 based on the error time setting information recorded in the recording unit 13. The collective setting display 55 includes displays of a type of a device, a function set in the device, a present setting value (a present value), and a setting value set by collective setting. The setting value is set according to an error state. Various setting values considered to be suitable for restoring the controlled devices 2 to the normal state from the error are displayed.

For example, about an electric knife, it is seen that a present effect mode is "1", a present output value is "13", an effect mode considered to be suitable for restoration from an error is "2", and an output value considered to be suitable for restoration from an error is "5". From display of the collective setting display 55, a surgeon can grasp setting states of the respective controlled devices 2 in an error occurrence state and relatively easily grasp information concerning setting values considered to be suitable for restoration from the error.

When agreeing to the setting values of the collective setting display 55, the surgeon operates the scope switch sw2. Consequently, the control unit 11 controls the respective units according to the setting values of the collective setting display 55. In this way, there is possibility that the controlled devices 2 can be restored to the normal state from the error in a short time only by operation of the scope switches sw by the surgeon. Alternatively, it is possible to perform setting for reducing adverse influence due to an error only with operation of the scope switches sw by the surgeon.

Note that when not agreeing to the setting values of the collective setting display 55, the surgeon operates the scope switch sw3. Consequently, the control unit 11 does not change the setting of the controlled devices 2. The screen changing unit 11c returns the display to the display before the scope switch sw1 is operated.

In this way, in the present embodiment, it is possible to obtain the same effects as the effects in the first embodiment. In the present embodiment, there is possibility that the surgeon or the like can easily confirm setting for facilitating the restoration from the error and the controlled devices 2 can be restored to the normal state from the error in a short time with simple operation.

Note that, as the collective setting screen, an example is explained in which only a set of setting values of one kind is displayed. However, when a plurality of sets of setting values are registered in the recording unit 13 as the error time setting information, for example, the function changing unit 11d may allocate a selecting function for the next set to the scope switch sw4 and the screen changing unit 11c may display the function allocated to the scope switch sw4 in the allocated display 34. In this case, with the operation of the scope switches sw, it is also possible to select an optimum set of setting values for restoring to the normal state from the error and cause the controlled devices 2 to execute the restoration to the normal state from the error.

Figure 11:
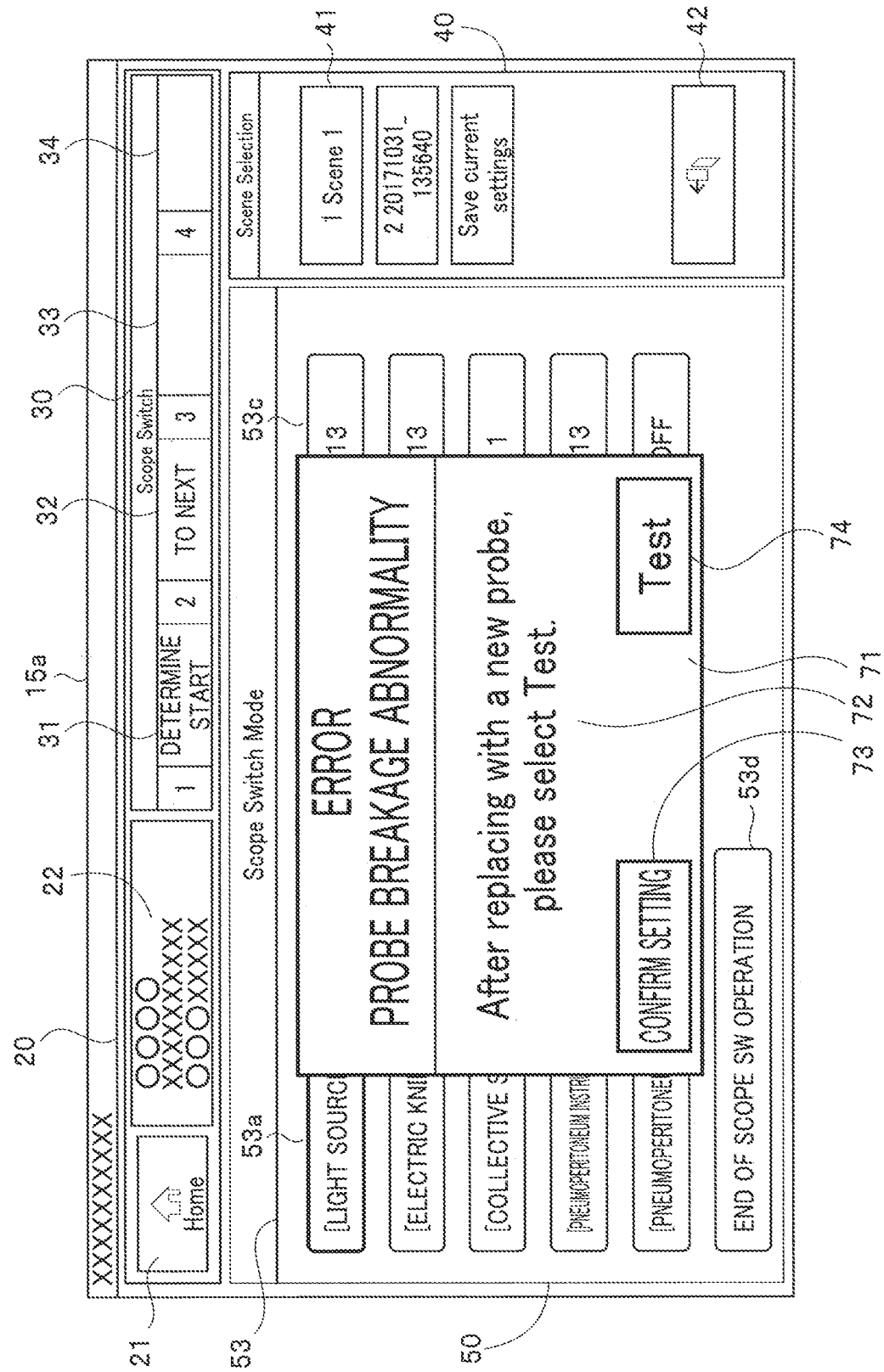
FIG. 11 is an explanatory diagram showing an example of an operation display in which an error popup display is displayed.

In the examples shown in FIG. 7 and FIG. 8, an example is explained in which the same moving (to next) function as the direction key is allocated to the scope switches sw. In the present embodiment, the moving function can be enabled about operation buttons on an error popup display. FIG. 11 is an explanatory diagram showing an example of an operation display in which such an error popup display is displayed. The example shown in FIG. 11 shows a state in which an error popup display 71 is displayed on the display of the setting screen shown in FIG. 8. The error popup display 71 includes a display 72 of error content, a setting confirmation button display 73, and a test button display 74. The display 72 includes a message indicating that an error is a breakage abnormality of a probe of the ultrasound coagulation cutting apparatus 2e and, for restoration from the error, Test only has to be selected after replacement of the probe with a new probe.

The user can switch selection of the setting confirmation button display 73 and the test button display 74 by operating the scope switch sw2. When the user operates the scope switch sw1 in a selected state of the setting confirmation button display 73, the control unit 11 can cause the operation panel 15 to display a display (not shown) for confirmation of a present setting state. After replacing the probe with the new probe, the user selects the test button display 74 with the scope switch sw2 and operates the scope switch sw1 in this selected state. Then, the control unit 11 can execute a test mode for detecting whether the breakage abnormality of the probe is eliminated and the controlled devices 2 return to the normal state from the error. Note that when the error detecting unit 11a detects with this test that the controlled devices 2 return to the normal state, the screen changing unit 11c erases the error popup display 71 and restores the original display.

Figure 12:
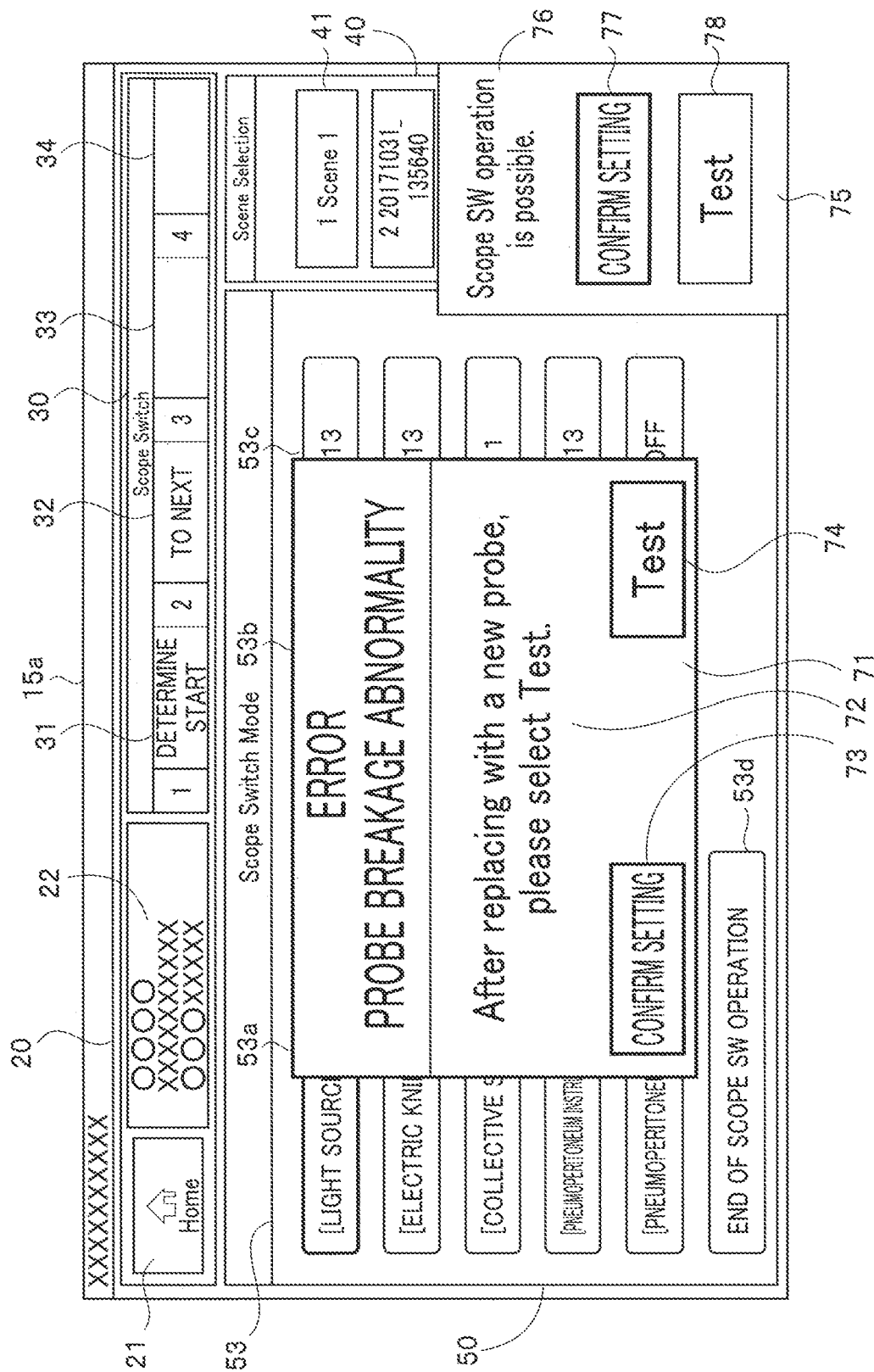
FIG. 12 is an explanatory diagram showing a display example of two error popup displays for touch operation and for operation of a scope switch sw.

FIG. 12 is an explanatory diagram showing a display example of two error popup displays for touch operation and for operation of the scope switches sw. In the example shown in FIG. 12, in the error popup display 71, the setting confirmation button display 73 and the test button display 74 are enabled by touching the display screen 15a of the operation panel 15. On the other hand, an error popup display 75 includes a display 76 of error content, a setting confirmation button display 77, and a test button display 78. The display 76 of error content corresponds to the display 72 of error content. The setting confirmation button display 77 corresponds to the setting confirmation button display 73. The test button display 78 corresponds to the test button display 74. Selection, movement, and execution of the setting confirmation button display 77 and the test button display 78 can be controlled by the scope switches sw.

In this way, in the examples shown in FIG. 11 and FIG. 12, operation making use of the scope switches sw is possible on the error popup display as well. The surgeon can easily perform operation for restoration from an error.

Third Embodiment

Figure 13:
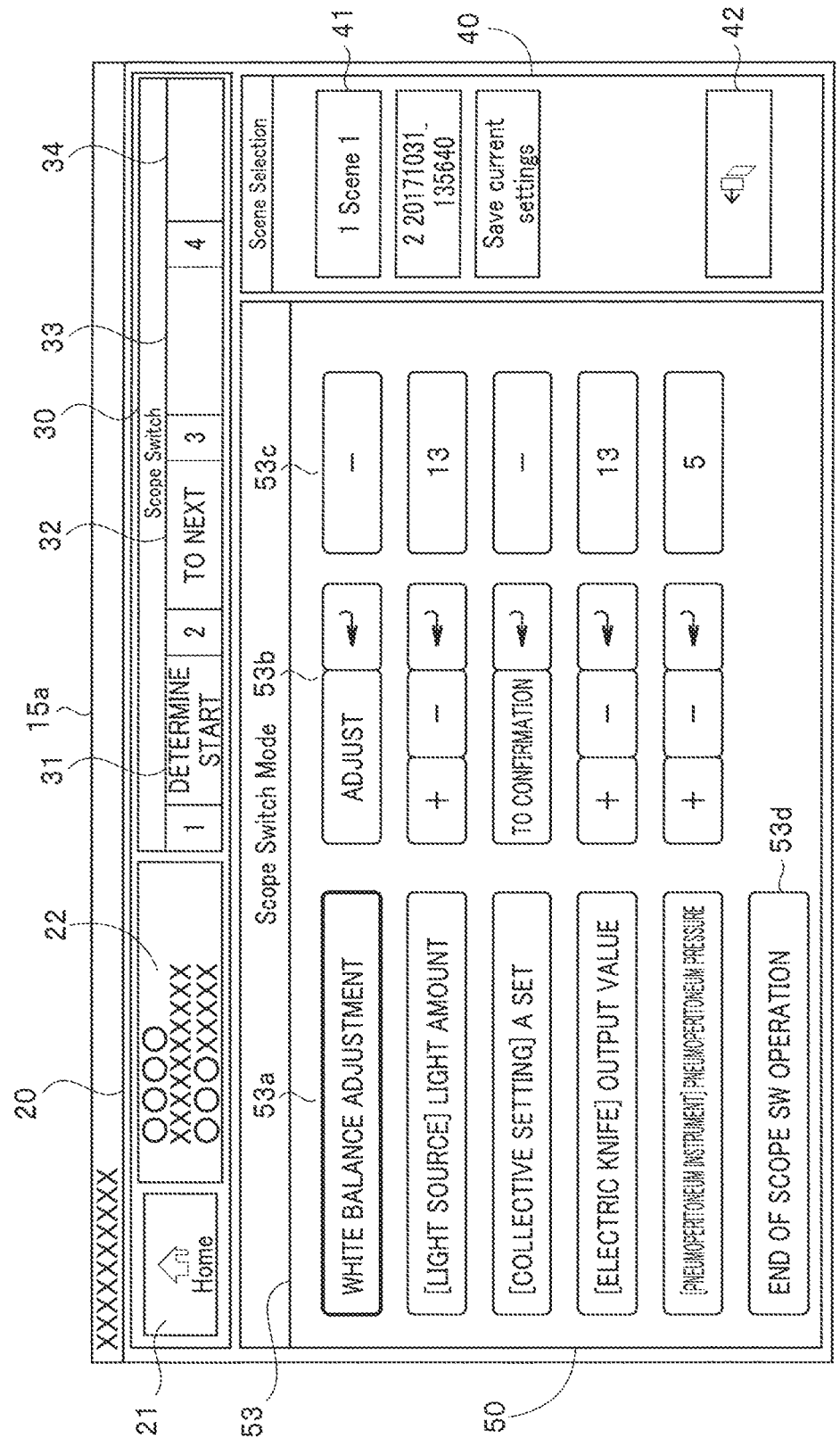
FIG. 13 is an explanatory diagram showing an example of a setting screen for various settings of the controlled devices 2.
Figure 14:
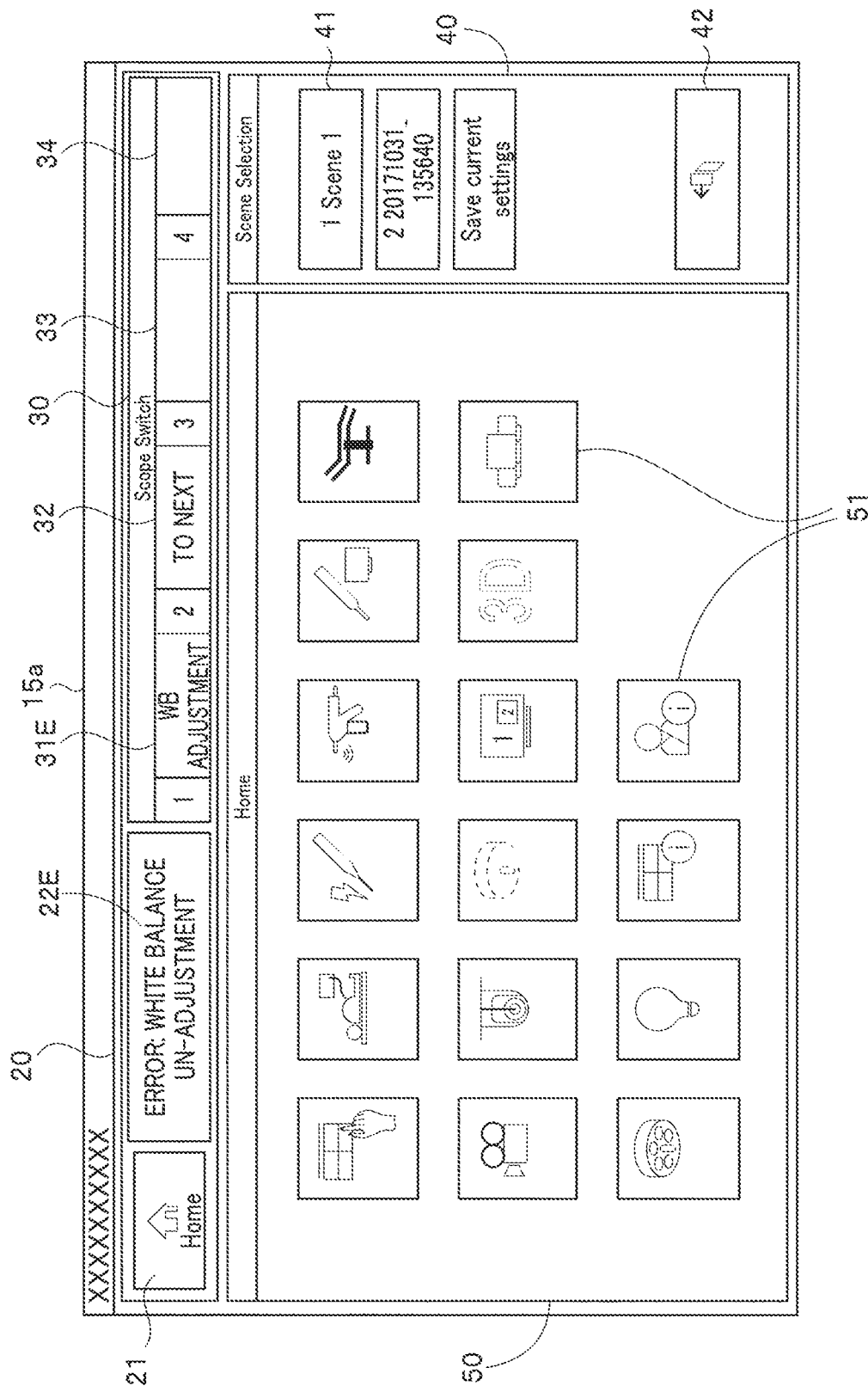
FIG. 14 is an explanatory diagram showing an example of a home screen at error occurrence time.

FIG. 13 and FIG. 14 relate to a third embodiment. FIG. 13 is an explanatory diagram showing an example of a setting screen for various settings of the controlled devices 2. FIG. 14 is an explanatory diagram showing an example of a home screen at error occurrence time. A hardware configuration in the present embodiment is the same as the hardware configuration shown in FIG. 1. Explanation about the hardware configuration is omitted. The present embodiment indicates operation display and allocated functions of the scope switches sw different from the operation display and the allocated functions in the first embodiment. The present embodiment facilitates white balance adjustment when a white balance is unadjusted.

(Normal State Time)

FIG. 13 shows the same setting screen as the setting screen shown in FIG. 8. In the example shown in FIG. 13, the setting display 53 includes, as setting targets, five setting target displays 53a for setting of white balance adjustment, setting of a light amount of a light source, collective setting by an A set, setting of an output value of an electric knife, and setting of a pneumoperitoneum pressure of a pneumoperitoneum instrument. When a user operates the scope switch sw1 in a state in which the white balance adjustment is selected as indicated by a thick frame in FIG. 13, selection moves to the button display 53b for adjustment. When the user operates the scope switch sw1 in a state in which adjustment among the button displays 53b is selected, the control unit 11 controls the respective units to execute the white balance adjustment. Consequently, it is possible to perform the white balance adjustment.

(Error Occurrence Time)

It is assumed that an adjustment error of a white balance is detected by the video processor 2a. When detecting based on information from the video processor 2a that the white balance is unadjusted, the error detecting unit 11a outputs a result of the detection to the screen changing unit 11c and the function changing unit 11d.

In this case, the function changing unit 11d changes the functions of the scope switches sw from the normal time allocated functions to the error time allocated functions. The screen changing unit 11c displays, as the display 22E of the upper side display region 20, a display (error: white balance unadjusted) indicating that an error has occurred and changes the scope switch display 30 to a display corresponding to the error time allocated functions.

FIG. 14 shows a display example in the case in which an adjustment error of the white balance occurs at display time of the home screen shown in FIG. 7. The example shown in FIG. 14 indicates that, at error occurrence time, in the allocated display 31E, a white balance adjustment (WB adjustment) function is set in the scope switch sw1. When the user operates the scope switch sw1, the control unit 11 controls the respective units to execute the white balance adjustment. Consequently, it is possible to perform the white balance adjustment.

In this way, in the present embodiment, the same effects as the effects in the first embodiment can be obtained. When an adjustment error of the white balance occurs, a user such as a doctor can easily carry out the white balance adjustment by operating the scope switches.

Fourth Embodiment

Figure 15:
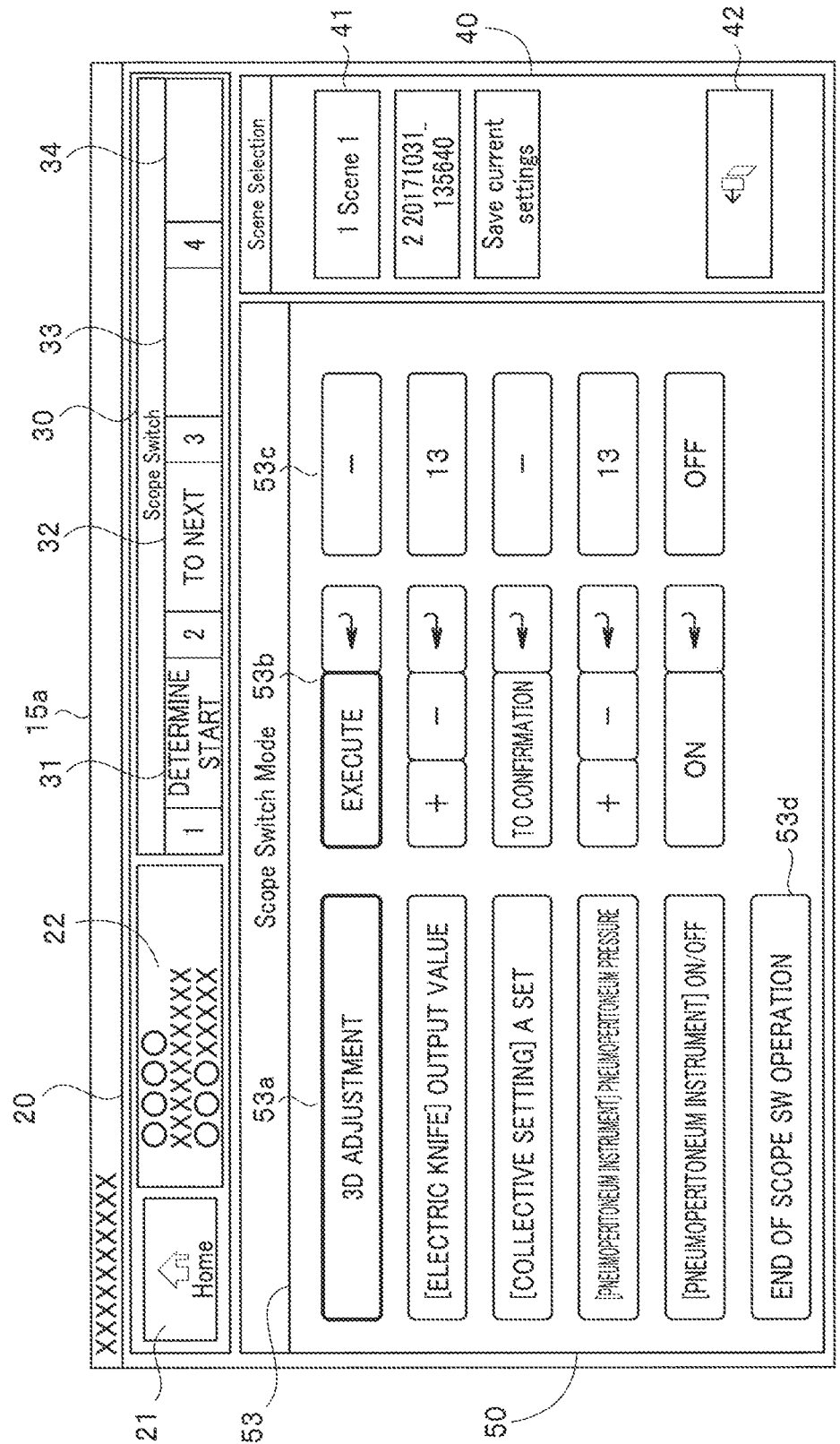
FIG. 15 is an explanatory diagram showing an example of a setting screen for various settings of the controlled devices 2.
Figure 16:
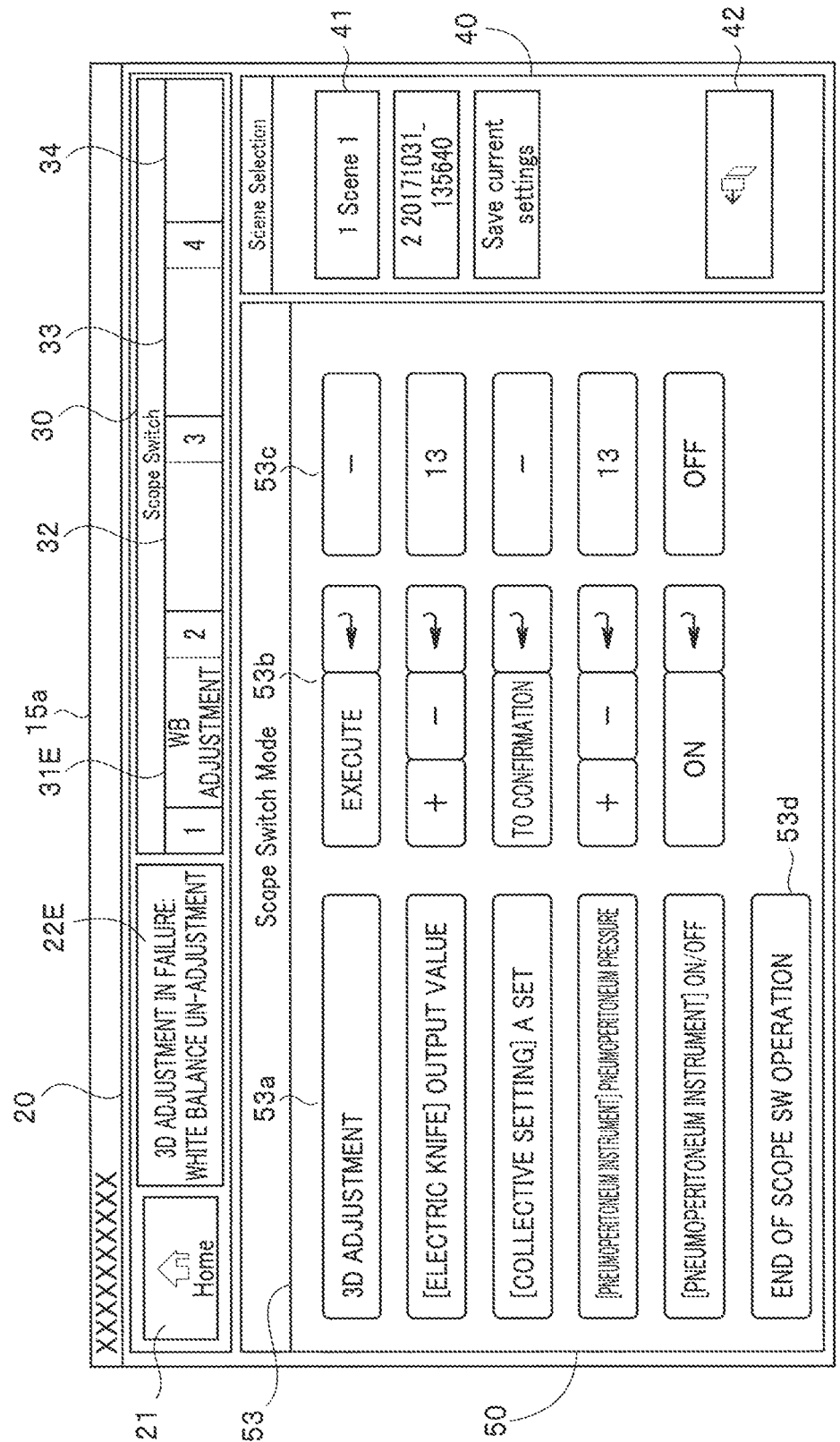
FIG. 16 is an explanatory diagram showing an example of a setting screen at error occurrence time.

FIG. 15 to FIG. 17 relate to a fourth embodiment of the present invention. FIG. 15 is an explanatory diagram showing an example of a setting screen for various settings of the controlled devices 2. FIG. 16 and FIG. 17 are explanatory diagrams showing examples of setting screens at error occurrence time. A hardware configuration in the present embodiment is the same as the hardware configuration shown in FIG. 1. Explanation about the hardware configuration is omitted. The present embodiment indicates an operation display and allocated functions of the scope switches sw different from the operation display and the allocated functions in the first embodiment. For example, when an error occurs because of a plurality of factors, depending on an occurrence state of an error, it is sometimes necessary to release the factors of the error occurrence in order for restoration from the error. The present embodiment is applied to such a case.

(Normal State Time)

FIG. 15 shows the same setting screen as the setting screen shown in FIG. 8. In the example shown in FIG. 15, the setting display 53 includes, as setting targets, five setting target displays 53a for setting of 3D adjustment, setting of an output value of an electric knife, collective setting by an A set, setting of a pneumoperitoneum pressure of a pneumoperitoneum instrument, and ON/OFF setting of the pneumoperitoneum instrument. When a user operates the scope switch sw1 in a state in which the 3D adjustment is selected as indicated by a thick frame in FIG. 15, selection moves to the button display 53b for execution. When the user operates the scope switch sw1 in a state in which execution among the button displays 53b is selected, the control unit 11 controls the respective units to execute the 3D adjustment. Consequently, it is possible to perform the 3D adjustment.

(Error Occurrence Time)

It is assumed that the 3D adjustment has ended in failure because of un-adjustment of a white balance. In this case, the video processor 2a detects the un-adjustment of the white balance and a 3D adjustment error. The error detecting unit 11a detects based on information from the video processor 2a that the 3D adjustment error has occurred because of the white balance un-adjustment and outputs a result of the detection to the screen changing unit 11c and the function changing unit 11d.

In this case, the function changing unit 11d changes the functions of the scope switches sw from the normal time allocated functions to the error time allocated functions. The screen changing unit 11c displays, as the display 22E of the upper side display region 20, a display indicating that the error has occurred (3D adjustment in failure: white balance un-adjustment) and changes the scope switch display 30 to a display corresponding to the error time allocated functions.

FIG. 16 shows a display example in the case in which a 3D adjustment error due to un-adjustment of the white balance occurs at display time of the setting screen shown in FIG. 15. The example shown in FIG. 16 indicates that, at error occurrence time, in the allocated display 31E, a white balance adjustment (WB adjustment) function is set in the scope switch sw1. When the user operates the scope switch sw1, the control unit 11 controls the respective units to execute white balance adjustment. Consequently, the white balance adjustment is performed.

The error detecting unit 11a detects with an output of the video processor 2a that the white balance adjustment is normally executed. At this point in time, the error detecting unit 11a also detects that a 3D adjustment error has occurred. The error detecting unit 11a gives a result of the detection to the screen changing unit 11c and the function changing unit 11d. Consequently, the function changing unit 11d changes the error time allocated functions according to a present state of the error and, for example, allocates the 3D adjustment function to the scope switch sw1. The screen changing unit 11c changes a display according to the present state of the error and the error time allocated functions allocated to the scope switches sw.

FIG. 17 shows display of the setting screen in this case. The display 22E is changed to 3D un-adjustment by the screen changing unit 11c. The allocated display 31E indicates that the white balance adjustment (WB adjustment) function is set in the scope switch sw1. When the user operates the scope switch sw1 in this state, the control unit 11 controls the respective units to execute 3D adjustment. Consequently, the 3D adjustment is performed. Note that when the 3D adjustment ends, the screen changing unit 11c returns the display of the operation panel 15 to the screen before the error detection (the setting screen shown in FIG. 15).

In this way, in the present embodiment, the same effects as the effects in the first embodiment can be obtained. In the present embodiment, when restoration from the error is possible by a series of processing, the functions allocated to the scope switches are changed for each kind of processing according to an occurrence state of the error. A user such as a doctor is capable of performing restoration from the error only by operating the scope switches, which leads to excellent convenience.

Among the techniques explained in the specification, the control mainly explained in the flowchart can often be set by a program and is sometimes stored in a recording medium or a recording unit. As a method of recording in the recording medium or the recording unit, the control may be recorded at a product shipment time, may be recorded using a distributed recording medium, or may be downloaded via the Internet.

The execution order of the steps in the flowchart may be changed, a plurality of the steps may be simultaneously executed, or the steps may be executed in different order in every execution unless contrary to natures of the steps.

Note that, in the embodiments, the portion described as "unit" may be configured by a dedicated circuit or may be configured by combining a plurality of general-purpose circuits or may be configured by combining, according to necessity, processors such as a microcomputer and a CPU that perform operation according to software programmed in advance or sequencers such as an FPGA.

The present invention is not limited to the respective embodiments per se. In an implementation stage, the constituent elements can be modified and embodied in a range not departing from the gist of the present invention. Various inventions can be formed by appropriate combinations of a plurality of constituent elements disclosed in the respective embodiments. For example, several constituent elements among all the constituent elements explained in the embodiments may be deleted. Further, the constituent elements in different embodiments may be combined as appropriate.

What is claimed is:

1. A central control apparatus comprising:
a processor comprising hardware, the processor being configured to:
set a first function allocated to one or more switches provided in a first medical instrument;
detect and display an occurrence of an error in at least one second medical device used in a medical procedure together with the first medical instrument, the at least one second medical device being different from the first medical instrument; and
reassign, based on the occurrence of the error, the first function allocated to the one or more switches provided on the first medical instrument to a second function, different from the first function, for processing the detected error in the at least one second medical device by operation of the one or more switches on the first medical instrument.

2. The central control apparatus according to claim 1, further comprising:
a display device configured to display an operation display for controlling the first medical instrument and the at least one second medical device and the display device being configured to display corresponding functions allocated to the one or more switches of the first medical instrument.

3. The central control apparatus according to claim 2, the processor is configured to change the operation display of the corresponding functions allocated to the one or more switches of the first medical instrument based on the the occurrence of the error.

4. The central control apparatus according to claim 3, wherein the processor changes the display to indicate the second function allocated to the one or more switches of the first medical instrument.

5. The central control apparatus according to claim 3, wherein the processor changes the instrument display based on a state of the detected error.

6. The central control apparatus according to claim 3, wherein the processor sets, as the second function to a function of performing operation for display in the operation display.

7. The central control apparatus according to claim 6, wherein the operation for the display in the operation display includes operation for moving and selecting a plurality of displays in the operation display and operation for executing the selected displays.

8. The central control apparatus according to claim 3, wherein the processor includes, as the second function for processing the error, a function of displaying a collective setting display for collectively performing setting of the at least one second medical device.

9. The central control apparatus according to claim 1, wherein the processor reassigns, according to a state of the detected error, the second function allocated to the one or more switches of the first medical instrument.

10. The central control apparatus according to claim 1, wherein the processor is further configured to reassign, when the detected error is processed, the second function allocated to the one or more switches provided on the first medical instrument back to the first function.

11. The central control apparatus according to claim 1, further comprising a recording apparatus configured to record, according to the occurrence of the error, setting information in which the second function allocated to the one or more switches of the first medical instrument is registered.

12. The central control apparatus according to claim 1, wherein the first medical instrument comprises an endoscope, the endoscope including the one or more switches.

13. The central control apparatus according to claim 12, wherein the at least one second medical device comprises a treatment device, the treatment device configured to treat a subject.

14. The central control apparatus according to claim 1, wherein the processor is configured to:
   determine that the detected error is processed when the second switch is pushed; and
   based on the determination, reassign the second function allocated to the one or more switches provided on the first medical instrument back to the first function.

15. A central control system comprising:
an endoscope; and
a central control apparatus comprising a processor comprising hardware, the processor is configured to:
   set a first function allocated to one or more switches provided in a first medical instrument;
   detect and display an occurrence of an error in at least one second medical device used in a medical procedure together with the first medical instrument, the at least one second medical device being different from the first medical instrument; and
   reassign, based on the occurrence of the error, the first function allocated to the one or more switches provided on the first medical instrument to a second function, different from the first function, for processing the detected error in the at least one second medical device by operation of the one or more switches on the first medical instrument.

16. The central control apparatus according to claim 15, wherein the at least one second medical device comprises a treatment device, the treatment device configured to treat a subject.

17. The central control system according to claim 15, wherein the processor is configured to:
   determine that the detected error is processed when the second switch is pushed; and
   based on the determination, reassign the second function allocated to the one or more switches provided on the first medical instrument back device to the first function.

18. A method for controlling a plurality of medical devices as controlled devices, the method comprising:
   setting a first function allocated to one or more switches provided in a first medical instrument;
   detecting and displaying occurrence of an error in at least one second medical device used in a medical procedure together with the first medical instrument, the at least one second medical device being different from the first medical instrument; and
   reassigning, based on the occurrence of the error, the first function allocated to the one or more switches provided on the first medical instrument to a second function, different from the first function, for processing the detected error in the at least one second medical device by operation of the one or more switches on the first medical instrument.

19. The method according to claim 18, wherein, further comprising returning the function allocated to the one or more switches to an original function before the reassigning after detecting that a normal state is restored from the error.

20. The method according to claim 18, further comprising:
   determining that the detected error is processed when the second switch is pushed; and
   based on the determination, reassigning the second function allocated to the one or more switches provided on the first medical instrument back to the first function.

* * * * *